United States Patent [19]
Schäfer et al.

[11] Patent Number: 5,661,107
[45] Date of Patent: Aug. 26, 1997

[54] HETEROCYCLIC COMPOUNDS AND THEIR USE AS HERBICIDES

[75] Inventors: Matthias Schäfer, Goldbach; Karlheinz Drauz, Freigericht, both of Germany

[73] Assignee: Degussa Aktiengesellschaft, Frankfurt am Main, Germany

[21] Appl. No.: 374,648

[22] PCT Filed: Jul. 29, 1993

[86] PCT No.: PCT/EP93/02027

§ 371 Date: Apr. 13, 1995

§ 102(e) Date: Apr. 13, 1995

[87] PCT Pub. No.: WO94/03459

PCT Pub. Date: Feb. 17, 1994

[30] Foreign Application Priority Data

Jul. 30, 1992 [DE] Germany .................. 42 25 167.2
Aug. 3, 1992 [DE] Germany .................. 42 25 629.1

[51] Int. Cl.⁶ .................. C07D 239/70; A01N 43/54
[52] U.S. Cl. .................. 504/240; 504/196; 504/197; 504/221; 504/224; 504/225; 544/52; 544/105; 544/116; 544/282; 544/278
[58] Field of Search .................. 544/282, 52, 105, 544/116; 504/240, 196, 197, 221, 224, 225

[56] References Cited

FOREIGN PATENT DOCUMENTS 0 272 594  6/1988  European Pat. Off. .

OTHER PUBLICATIONS

George DeStevens et al., "Investigations in Heterocycles. XV. Methylphenidate: A Versatile Intermediate in the Synthesis of Bicyclic Heterocycles with a Bridgehead Nitrogen Atom", *Journal of Medicinal Chemistry*, 1964, pp. 146–149.

M. Y. Ebeid et al., "Synthesis of some pyrrolo [1,2-c] pyrimidines of potential pharmacological interest", *Chemical Abstracts*, Abstract No. 192762j, vol. 110, No. 21, 1989.

"Imidazopyrimidines", *Chemical Abstracts*, Abstract No. 139965f, vol. 99, No. 17, 1983.

*Primary Examiner*—John M. Ford
*Attorney, Agent, or Firm*—Cushman Darby & Cushman, IP Group of Pillsbury Madison & Sutro LLP

[57] ABSTRACT

Compounds of the formula

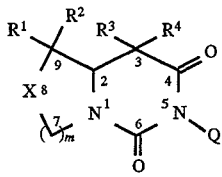

wherein m represents 1 or 2, X represents O, S, $CH_2$ or substituted $CH_2$, $R_1$–$R_4$ represent hydrogen or substituted or unsubstituted hydrocarbon groups, and Q represents a substituted phenyl group. These compounds are useful as herbicides and are active in small doses with high selectivity between useful plants and weeds.

6 Claims, No Drawings

HETEROCYCLIC COMPOUNDS AND THEIR USE AS HERBICIDES

This application is made under 35 USC § 371, based on PCT/EP93/02027, filed Jul. 29, 1993.

BACKGROUND OF THE INVENTION

1. Field of the Invention

The present invention relates to new types of heterocyclic compounds of the formula I

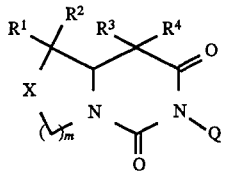

which m, X, $R^1$, $R^2$, $R^3$, $R^4$, and Q have the meaning mentioned in the description, a method for their preparation and their use as herbicides.

2. Description of Related Art

As has already been communicated, specific uracil derivatives (see U.S. Pat. No. 4,943,309) or heterocyclic imides (see EP-A1 272 594, EP-B1 0 070 389) can be used as herbicides.

Surprisingly, new types of heterocyclic compounds have now been found, which have a clearly improved herbicidal effect and outstanding selectivity.

SUMMARY OF THE INVENTION

The present invention therefore provides compounds of the formula I, in which

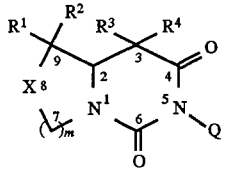

X represents O, S, $CH_2$, CHF, $CF_2$, CHCl, CHBr, $CHOCH_2F$, $CHOCF_3$ or $CHOCH_2CF_3$, m represents 1 or 2

$R^1$ and $R^2$, independently of each other, represent hydrogen, hydroxy, a halogen, or a $(C_1-C_4)$-alkyl, $(C_1-C_4)$-alkoxy, $(C_1-C_4)$-haloalkyl or $(C_1-C_4)$-haloalkoxy group, $R^3$ and $R^4$, independently of each other, represent hydrogen, hydroxy, a halogen, cyanogen, a $(C_1-C_4)$-alkyl, $(C_1-C_4)$-haloalkyl, $(C_3-C_4)$-alkenyl, $(C_3-C_4)$-haloalkenyl, $(C_1-C_4)$-alkoxy, $(C_2-C_6)$-alkoxycarbonyl, or $(C_3-C_8)$-alkoxycarbonylalkyl group or phenyl or benzyl, both optionally substituted by halogen or a $(C_1-C_4)$-alkyl or $(C_1-C_4)$-alkoxy group, Q represents one of the groups Q-1–Q-7,

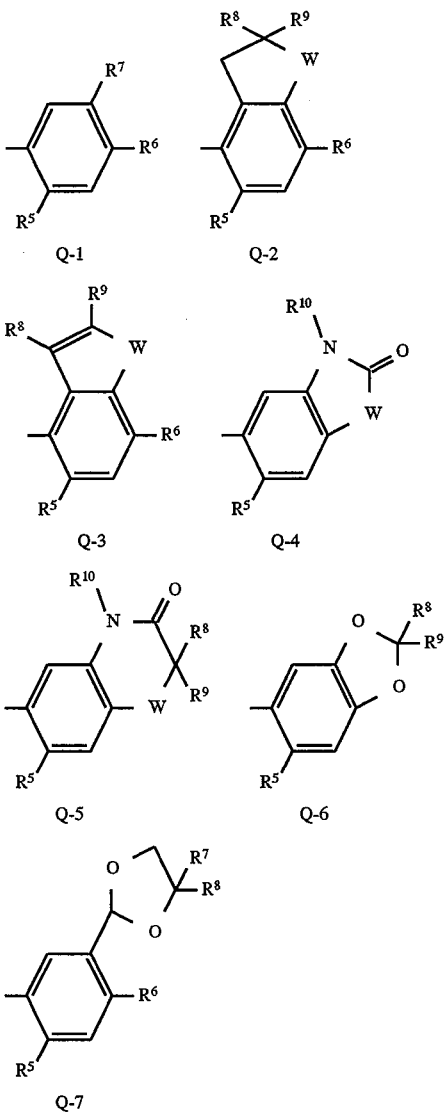

in which
w represents O or S,
$R^5$ represents hydrogen or a halogen,
$R^6$ represents a $(C_1-C_4)$-alkyl or $(C_1-C_2)$-haloalkyl group, $OCH_3$, $SCH_3$, $OCHF_2$, a halogen, CN or $NO_2$,
$R^7$ represents hydrogen or a $(C_1-C_8)$-alkyl or $(C_1-C_8)$-haloalkyl group, a halogen, $OR^{11}$, $S(O)_nR^{11}$, $COR^{11}$, $CO_2R^{11}$, $C(O)SR^{11}$, $C(O)NR^{12}R^{13}$, CHO, $CH=CHCO_2R^{11}$, $CO_2N=CR^{14}R^{15}$, $NO_2$, CN, $NHSO_2R^{16}$ or $NHSO_2NHR^{16}$,
$R^8$ represents hydrogen, a $(C_1-C_3)$-alkyl or $(C_1-C_3)$-haloalkyl group or a halogen,
$R^9$ represents hydrogen, a $(C_1-C_3)$-alkyl or $(C_1-C_3)$-haloalkyl group or a halogen; or, when Q is Q-2 or Q-6, $R^8$ and $R^9$, together with the carbon atom to which they are bonded, may be C=O,
$R^{10}$ represents a $(C_1-C_6)$-alkyl, $(C_1-C_6)$-haloalkyl, $(C_2-C_6)$-alkoxyalkyl, $(C_3-C_6)$-alkenyl or $(C_3-C_6)$-alkynyl group,
$R^{11}$ represents a $(C_1-C_8)$-alkyl, $(C_3-C_8)$-cycloalkyl, $(C_3-C_8)$-alkenyl, $(C_3-C_8)$-alkynyl, $(C_1-C_8)$-haloalkyl, $(C_2-C_8)$-alkoxyalkyl, $(C_2-C_8)$-alkylthioalkyl, $(C_2-C_8)$ -alkylsulphinylalkyl, $(C_2-C_8)$-alkylsulphonylalkyl, $(C_4-C_8)$-alkoxyalkoxyalkyl, $(C_4-C_8)$-cycloalkylalkyl, $(C_2-C_4)$-carboxyalkyl, $(C_3-C_8)$-alkoxycarbonylalkyl, $(C_6-C_8)$-alkenyloxycarbonylalkyl $(C_6-C_8)$-alkynyloxycarbonylalkyl, $(C_4-C_8)$-alkenoxyalkyl, $(C_6-C_8)$-cycloalkoxyalkyl, $(C_4-C_8)$-alkynyloxyalkyl, $(C_3-C_8)$-haloalkoxyalkyl, $(C_4-C_8)$-haloalkenyloxyalkyl, $(C_4-C_8)$-haloalkynyloxyalkyl, $(C_6-C_8)$-cycloalkythioalkyl, $(C_4-C_8)$-alkenylthioalkyl, $(C_4-C_8)$-alkynylthioalkyl, $(C_1-C_4)$-alkyl substituted with phenoxy or benzyloxy, both optionally substituted with halogen or a $(C_1-C_3)$-alkyl or $(C_1-C_3)$-haloalkyl group, $(C_4-C_8)$-trialkylsilylalkyl, $(C_3-C_8)$-cyanoalkyl, $(C_3-C_8)$-halocycloalkyl, $(C_3-C_8)$-haloalkenyl, $(C_5-C_8)$-alkoxyalkenyl, $(C_5-C_8)$-haloalkoxyalkenyl, $(C_5-C_8)$-alkylthioalkenyl, $(C_3-C_8)$-haloalkynyl, $(C_5-C_8)$-alkoxyalkynyl, $(C_5-C_8)$-haloalkoxyalkynyl, $(C_5-C_8)$-alkylthioalkynyl or $(C_2-C_8)$-alkylcarbonyl group, benzyl, optionally substituted with halogen or a $(C_1-C_3)$-alkyl or $(C_1-C_3)$-haloalkyl group, $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CR^{17}C(O)NH_2$, phenyl or pyridyl, both optionally substituted with halogen or a $(C_1-C_3)$-alkyl, $(C_1-C_3)$-haloalkyl or $(C_1-C_4)$-alkoxy group, $R^{12}$ and $R^{14}$, independently of each other, represent hydrogen or a $(C_1-C_4)$-alkyl group, $R^{13}$ and $R^{15}$, independently of each other, represent a $(C_1-C_4)$-alkyl group or phenyl, optionally substituted with halogen or a $(C_1-C_3)$-alkyl, $(C_1-C_3)$-haloalkyl or $(C_1-C_4)$-alkoxy group, $R^{12}$ and $R^{13}$, when they are $-(CH_2)_5-$, $-(CH_2)_4-$ or $-CH_2CH_2OCH_2CH_2-$, may be combined to give rings, wherein one or more H atoms in each ring may optionally be substituted by a $(C_1-C_3)$-alkyl group, phenyl or benzyl, $R^{14}$ and $R^{15}$, together with the carbon atom to which they are bonded, may form a $(C_3-C_8)$-cycloalkyl group, $R^{16}$ represents a $(C_1-C_4)$-alkyl or $(C_1-C_4)$-haloalkyl group, $R^{17}$ represents hydrogen or a $(C_1-C_3)$-alkyl group, $R^{18}$ represents a $(C_1-C_6)$-alkyl, $(C_3-C_6)$-alkenyl or $(C_3-C_6)$-alkynyl group and n represents 0, 1 or 2.

In the definitions given above, the term "alkyl", on its own or in combination names such as "alkylthio" or "haloalkyl", comprises straight-line or branched chains, e.g. methyl, ethyl, n-propyl, isopropyl or the various butyl isomers. Alkoxy comprises methoxy, ethoxy, n-propyloxy, isopropyloxy and the various butyloxy isomers. Alkenyl comprises straight-line or branched alkenes, e.g. 1-propenyl, 2-propenyl, 3-propenyl and the various butenyl isomers. Cycloalkyl comprises cyclopropyl, cyclobutyl, cyclopentyl and cyclohexyl. The term "halogen" on its own or in combination terms such as "haloalkyl" means fluorine, chlorine, bromine or iodine. Furthermore, when "haloalkyl" is used in the combination terms, then the alkyl may be partially or fully substituted with halogen atoms, which for their part may be identical or different. $CH_2CH_2F$, $CF_2CF_3$ and $CH_2CHFCl$ are examples of haloalkyl groups.

The following groups are preferred, in which

X represents O, S, $CH_2$, CHF, $CF_2$, CHCl, CHBr, $CHOCHF_2$, $CHOCF_3$ or $CHOCH_2CF_3$, m represents 1 or 2, $R^1$ and $R^2$, independently of each other, represent hydrogen, hydroxy, fluorine, chlorine, bromine, methyl or methoxy, $R^3$ and $R^4$, independently of each other, represent hydrogen, hydroxy, fluorine, chlorine, bromine, cyanogen, a $(C_1-C_2)$-alkyl, $(C_1-C_2)$-haloalkyl, $(C_3-C_4)$-alkenyl, $(C_3-C_4)$-haloalkenyl or $(C_1-C_2)$-alkoxy group or phenyl or benzyl, both optionally substituted with fluorine, chlorine, bromine, methyl or methoxy, Q represents

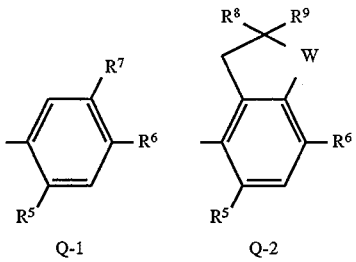

Q-1    Q-2

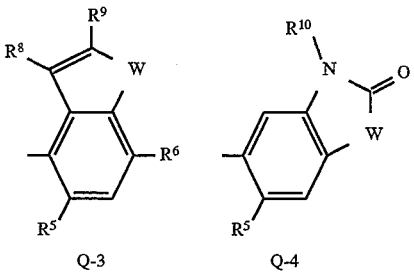

Q-3    Q-4

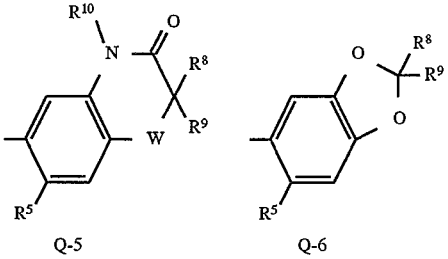

Q-5    Q-6

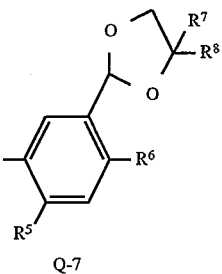

Q-7 in which, w represents O or S, n represents 0, 1 or 2, $R^5$ represents hydrogen or a halogen, $R^6$ represents a halogen or CN, $R^7$ represents hydrogen, a $(C_1-C_4)$-alkyl or $(C_1-C_4)$-haloalkyl group, a halogen, $OR^{11}$, $S(O)_nR^{11}$, $COR^{11}$, $CO_2R^{11}$, $C(O)SR^{11}$, $C(O)NR^{12}R^{13}$, $CH=CHCO_2R^{11}$, $CO_2N=CR^{14}R^{15}$, $NHSO_2R^{16}$ or $NHSO_2NHR^{16}$, $R^8$ represents hydrogen or a $(C_1-C_3)$-alkyl or $(C_1-C_3)$-haloalkyl group, $R^9$ represents hydrogen or a $(C_1-C_3)$-alkyl or $(C_1-C_3)$-haloalkyl group, or, when Q=Q-2 or Q-6, $R^8$ and $R^9$, together with the carbon to which they are bonded, may be C=O, $R^{10}$ represents a $(C_1-C_4)$-alkyl, $(C_1-C_4)$-haloalkyl, $(C_2-C_4)$-alkoxyalkyl, $(C_3-C_6)$-alkenyl or $(C_3-C_6)$-alkynyl group, $R^{11}$ represents a $(C_1-C_4)$-alkyl, $(C_3-C_6)$-cycloalkyl, $(C_3-C_6)$-alkenyl, $(C_3-C_6)$-alkynyl, $(C_1-C_4)$-haloalkyl, $(C_2-C_4)$-alkoxyalkyl, $(C_2-C_4)$-alkylthioalkyl, $(C_2-C_4)$-alkylsulphinylalkyl, $(C_2-C_4)$-alkylsulphonylalkyl, $(C_3-C_6)$-alkoxyalkoxyalkyl, $(C_4-C_8)$-cycloalkylalkyl, $(C_2-C_4)$-carboxyalkyl, $(C_3-C_6)$-alkoxycarbonylalkyl, $(C_6-C_8)$-alkenyloxycarbonylalkyl $(C_6-C_8)$-alkynyloxycarbonylalkyl, $(C_4-C_6)$-alkenoxyalkyl, $(C_6-C_8)$-cycloalkoxyalkyl, $(C_4-C_6)$-alkynyloxyalkyl, $(C_3-C_6)$-haloalkoxyalkyl, $(C_4-C_8)$-haloalkenyloxyalkyl, $(C_4-C_6)$-haloalkynyloxyalkyl, $(C_6-C_8)$-cycloalkylthioalkyl, $(C_4-C_6)$-alkenylthioalkyl, $(C_4-C_6)$-alkynylthioalkyl, $(C_1-C_2)$-alkyl substituted with phenoxy or benzyloxy, both optionally substituted with halogen, $(C_1-C_3)$-alkyl or $(C_1-C_3)$-haloalkyl group, $(C_4-C_8)$-trialkylsilylalkyl, $(C_3-C_4)$-cyanoalkyl, $(C_3-C_6)$-halocycloalkyl, $(C_3-C_6)$-haloalkenyl, $(C_5-C_6)$-haloalkoxyalkenyl, $(C_5-C_6)$-alkylthioalkenyl, $(C_3-C_6)$-haloalkynyl, $(C_5-C_6)$-alkoxyalkynyl, $(C_5-C_6)$-haloalkoxyalkynyl, $(C_5-C_6)$-alkylthioalkynyl or $(C_2-C_4)$-alkylcarbonyl group, benzyl, optionally substituted with alkyl, $(C_2-C_4)$-alkylsulphonylalkyl, $(C_3-C_6)$-alkoxyalkoxyalkyl, $(C_4-C_8)$-cycloalkylalkyl, $(C_2-C_4)$-carboxyalkyl, $(C_3-C_6)$-alkoxycarbonylalkyl, $(C_6-C_8)$-alkenyloxycarbonylalkyl $(C_6-C_8)$-alkynyloxycarbonylalkyl, $(C_4-C_6)$-alkenoxyalkyl, $(C_6-C_8)$-cycloalkoxyalkyl, $(C_4-C_6)$-alkynyloxyalkyl, $(C_3-C_6)$-haloalkoxyalkyl, $(C_4-C_8)$-haloalkenyloxyalkyl, $(C_4-C_6)$-haloalkynyloxyalkyl, $(C_6-C_8)$-cycloalkylthioalkyl, $(C_4-C_6)$-alkenylthioalkyl, $(C_4-C_6)$-alkynylthioalkyl, $(C_1-C_2)$-alkyl substituted with phenoxy or benzyloxy, both optionally substituted with halogen or a $(C_1-C_3)$-alkyl or $(C_1-C_3)$-haloalkyl group, $(C_4-C_8)$-trialkylsilylalkyl, $(C_3-C_4)$-cyanoalkyl, $(C_3-C_6)$-halocycloalkyl, $(C_3-C_6)$-haloalkenyl, $(C_5-C_6)$-haloalkoxyalkenyl, $(C_5-C_6)$-alkylthioalkenyl, $(C_3-C_6)$-haloalkynyl, $(C_5-C_6)$-alkoxyalkynyl, $(C_5-C_6)$-haloalkoxyalkynyl, $(C_5-C_6)$-alkylthioalkynyl or $(C_2-C_4)$-alkylcarbonyl group, benzyl, optionally substituted with halogen or a $(C_1-C_2)$-alkyl or $(C_1-C_2)$-haloalkyl group, $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CHR^{17}C(O)NH_2$, phenyl or pyridyl, both optionally substituted with halogen or a $(C_1-C_3)$-alkyl, $(C_1-C_3)$-haloalkyl or $(C_1-C_4)$-alkoxy group, $R^{12}$ and $R^{14}$, independently of each other, represent hydrogen or a $(C_1-C_2)$-alkyl group, Q represents

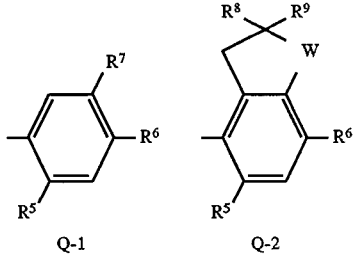

Q-1　　　Q-2

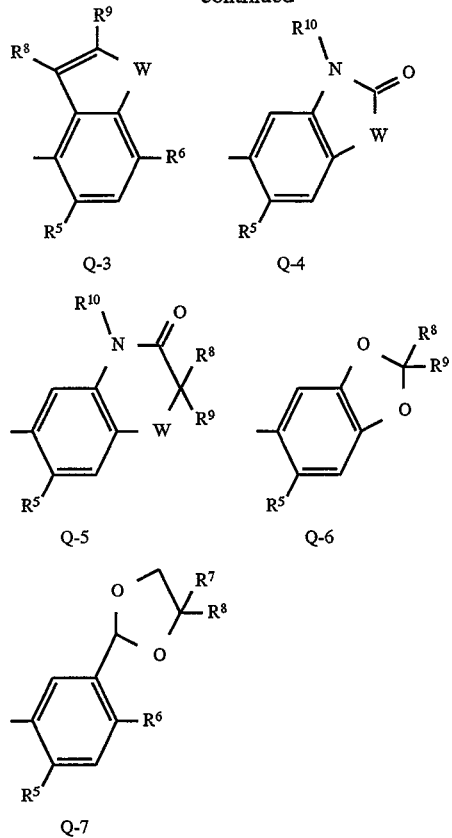

Q-3　　　Q-4

Q-5　　　Q-6

Q-7 in which w represents O or S, $R^5$ represents hydrogen, fluorine or chlorine, $R^6$ represents chlorine, bromine or cyanogen, $R^7$ represents hydrogen, $OR^{11}$ or $CO_2R^{11}$, $R^8$ and $R^9$, independently of each other, represent hydrogen or a $(C_1-C_2)$-alkyl or $(C_1-C_2)$-haloalkyl group, $R^{10}$ represents a $(C_1-C_2)$-alkyl, $(C_1-C_2)$-haloalkyl, $(C_3-C_4)$-alkenyl or $(C_3-C_4)$-alkynyl group, $R^{11}$ represents a $(C_1-C_4)$-alkyl, $(C_3-C_6)$-cycloalkyl, $(C_3-C_6)$-alkenyl, $(C_3-C_6)$-alkynyl, $(C_1-C_4)$-haloalkyl, $(C_2-C_4)$-alkoxyalkyl, $(C_2-C_4)$-alkylthioalkyl, $(C_2-C_4)$-alkylsulphinylalkyl, $(C_2-C_4)$-alkylsulphonylalkyl, $(C_3-C_6)$-alkoxyalkoxyalkyl, $(C_4-C_8)$-cycloalkylalkyl, $(C_2-C_4)$-carboxyalkyl, $(C_3-C_6)$-alkoxycarbonylalkyl, $(C_6-C_8)$-alkenyloxycarbonylalkyl $(C_6-C_8)$-alkynyloxycarbonylalkyl, $(C_6-C_8)$-cycloalkoxyalkyl, $(C_4-C_6)$-alkenyloxyalkyl, $(C_4-C_6)$-alkynyloxyalkyl, $(C_3-C_6)$-haloalkoxyalkyl, $(C_4-C_8)$-haloalkenoxyalkyl, $(C_4-C_6)$-haloalkynyloxyalkyl, $(C_6-C_8)$-cycloalkylthioalkyl, $(C_4-C_6)$-alkenylthioalkyl, $(C_4-C_6)$-alkynylthioalkyl, $(C_1-C_2)$-alkyl substituted with phenoxy or benzyloxy, both optionally substituted with halogen or a $(C_1-C_3)$-alkyl or $(C_1-C_3)$-haloalkyl group, $(C_4-C_8)$-trialkylsilylalkyl, $(C_3-C_4)$-cyanoalkyl, $(C_3-C_6)$-halocycloalkyl, $(C_3-C_6)$-haloalkenyl, $(C_5-C_6)$-alkoxyalkenyl, $(C_5-C_6)$-haloalkoxyalkenyl, $(C_5-C_6)$-alkylthioalkenyl, $(C_3-C_6)$-haloalkynyl, $(C_5-C_6)$-alkoxyalkynyl, $(C_5-C_6)$-haloalkoxyalkynyl, $(C_5-C_6)$-alkylthioalkynyl or $(C_2-C_4)$-alkylcarbonyl group, benzyl, optionally substituted with halogen or a $(C_1-C_2)$-alkyl or $(C_1-C_2)$-haloalkyl group, $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CR^{17}C(O)NH_2$, phenyl or pyridyl, both optionally substituted with fluorine, chlorine or bromine or a $(C_1-C_2)$-haloalkyl or $(C_1-C_2)$-alkoxy group, $R^{12}$ represents hydrogen or a $(C_1-C_2)$-alkyl group, $R^{13}$ represents a $(C_1-C_2)$-alkyl group, phenyl, optionally substituted with fluorine, chlorine, bromine or a $(C_1-C_2)$-alkyl, $(C_1-C_2)$-haloalkyl or $(C_1-C_2)$-alkoxy group, $R^{12}$ and $R^{13}$, when they are $-(CH_2)_5-$, $-(CH_2)_4-$ or $-CH_2CH_2OCH_2CH_2-$, may be combined to give rings, wherein one or more H atoms in each ring may optionally be substituted by a $(C_1-C_2)$-alkyl group, $R^{17}$ represents hydrogen or a $(C_1-C_2)$-alkyl group and $R^{18}$ represents a $(C_1-C_2)$-alkyl, $(C_3-C_4)$-alkenyl or $(C_3-C_4)$-alkynyl group.

The following groups are particularly preferred, in which
X represents $CH_2$, O or S,
m represents 1 or 2,
$R^1$ and $R^2$ represent hydrogen,
$R^3$ and $R^4$ represent hydrogen,
Q represents

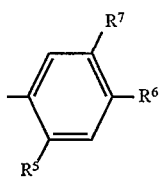

Q-1 in which,
$R^5$ represents fluorine or chlorine,
$R^6$ represents chlorine,
$R^7$ represents $OR^{11}$ or $CO_2R^{11}$ and
$R^{11}$ represents a $(C_1-C_4)$-alkyl, $(C_3-C_6)$-cycloalkyl, $(C_3-C_6)$-alkenyl, $(C_3-C_4)$-alkynyl, $(C_1-C_3)$-haloalkyl, $(C_2-C_4)$-alkoxyalkyl, $(C_3-C_6)$-alkoxycarbonylalkyl, $(C_6-C_8)$-alkenyloxycarbonylalkyl or $(C_6-C_8)$-alkynyloxycarbonyl group.

The invention relates to both the individual stereoisomers of the formula I which are possible and also to mixtures of these isomers The new types of heterocyclic compounds of the general formula I are obtained by the present invention when aryl isocyanates of the general formula II

   II in which,
Q is defined as above, react with carboxylic acids or their esters of the general formula III

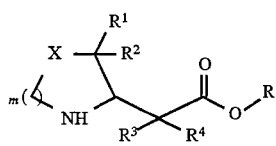   III in which m, X, $R^1$, $R^2$, $R^3$ and $R^4$ are defined as above, and R represents hydrogen, a $(C_1-C_4)$-alkyl group or an active ester, in accordance with method A, optionally in the presence of an acid acceptor and optionally in the presence of a diluent.

The invention also provides a method B for preparing compounds of the formula I by means of a reaction between compounds of the general formula IV

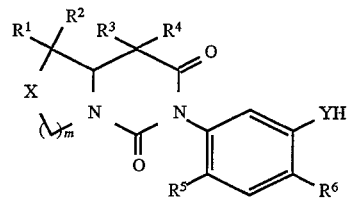   IV in which, X, $R^1$, $R^2$, $R^3$ and $R^4$ are defined as above and Y=O, S or NH; and a halide of the formula V, VI or VII,

   V

   VI

   VII in which Z is a chlorine, bromine or iodine atom and $R^{11}$ and $R^{16}$ are defined as above.

The invention also provides a method C for preparing compounds of the formula I, which is explained in the following; wherein m, X, $R^1$, $R^2$, $R^3$, $R^4$ and Q are defined as above.

In this case, a compound of the formula III, in which R=H or a $(C_1-C_4)$-alkyl group, reacts with phosgene or a phosgene substitute, wherein initially compounds of the formula VIII are produced and these then react with compounds of the formula IX to give compounds of the formula X,

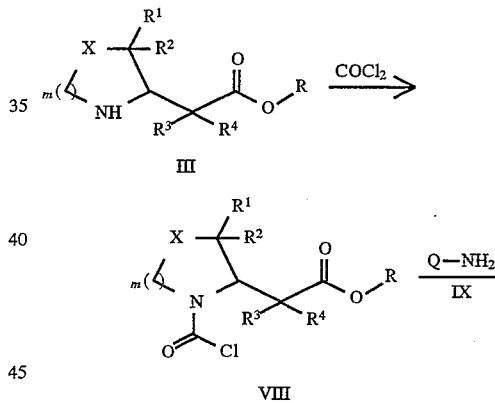

prior to converting a compound of the formula X into compounds of the formula I by ring-closure.

The invention also provides a method D for preparing compounds of the formula I, which is explained in the following, wherein m, X, $R^1$, $R^2$, $R^3$, $R^4$ and Q are defined as above and wherein a compound of the formula II reacts with a compound of the formula XI, optionally in the presence of an acid acceptor and optionally in the presence of a diluent, that compounds of the formula XII are thereby produced and that the compounds XII thereby obtained are then hydrolysed and converted into compounds of the formula I by ring-closure.

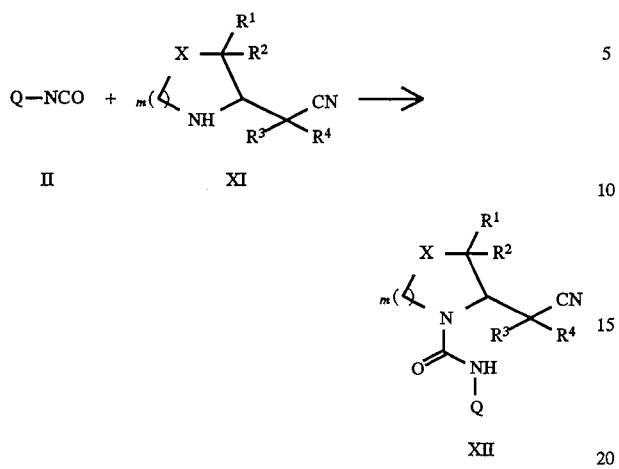

In the case of method A, when R=alkyl, the reaction is performed in an inert organic solvent, for example in an aromatic solvent such as toluene or chlorobenzene, a halogenated hydrocarbon such as chloroform or methylene chloride, an ether such as diisopropyl ether or in acetonitrile or dimethyl-formamide, optionally base-catalysed, at temperatures between 20° and 125° C. Organic bases are preferably used as bases, for example organic amines such as triethylamine or pyridine.

In the vent that R=H, the reaction is performed in water as a solvent or, preferably, in a two-phase water/organic solvent system. Particularly preferred is the method of working in which a compound of the formula III, optionally a salt of III, is added to water together with an inorganic base, for example an alkali metal or alkaline earth metal hydroxide, carbonate or hydrogen carbonate, such as sodium hydroxide or potassium carbonate, or together with an organic base such as, for example, an organic amine such as triethylamine, and then compounds of the formula II, dissolved in an inert solvent such as, for example, toluene, chlorobenzene or chloroform, are introduced. The reaction mixture is then maintained at temperatures between −40° C. and +50° C., preferably between −10° C. and +10° C., for several days, preferably between 3 and 50 h.

The aqueous phase is then adjusted to a pH between 1 and 3 with acid, preferably an inorganic acid such as aqueous hydrochloric or sulphuric acid. The urea derivatives produced in this way (see compounds X) are then cyclised at temperatures between 50° and 100° C., optionally in the presence of an acid such as hydrochloric acid and/or formic acid, or optionally by conversion into an ester (R=alkyl or active ester, e.g. an O-succinimide ester or anhydride ester) using known methods (see Houben-Weyl, "Methoden der organischen Chemie", vol. XXV/1 and XXV/2 (1974)).

Compounds of the formula II are known or may be prepared by analogy with known methods, see Houben-Weyl, "Methoden der organischen Chemie", vol. VIII, p. 120 (1952); Houben-Weyl, vol. IX, pp. 875, 869 (1955); EP-B1 0 070 389; U.S. Pat. No. 4,881,967; EP-A1 322 401; U.S. Pat. No. 3,495,967; EP-A-2 300 307; EP-A2 349 832.

Amines of the formula III are known and may be prepared by analogy with known methods; see here, for example, M. Sekiya et al., Chem. Pharm. Bull. 31 (1) 94 (1983); J. M. Cassal. A. Fürst, W. Meier, Helv. Chim. Acta, 59 (6) 1917 (1976); S.-K. Tsui, J. D. Wood, Can. J. Chem., 57 (15) 1977 (1979); M. Sekiya et al., Chem. Lett., (2) 231 (1982).

Finally, it was found that the new types of heterocyclic compounds of the general formula I have remarkable herbicidal properties.

The invention therefore also relates to herbicidal compositions which contain an effective amount of a compound of the formula I and a carrier. Carriers are advantageously surface active substances or solid or liquid diluents.

The invention also relates to a process for controlling weeds in which a herbicidally effective amount of a compound in accordance with formula I is applied to the weeds or their surroundings (before or after germination).

DETAILED DESCRIPTION OF THE INVENTION

CHEMICAL EXAMPLES

Example 1

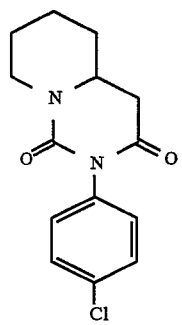

A mixture of methyl 2-piperidinacetate (1.94 g, 0.1 mol), triethylamine (50.0 mg, 0.5 mmol) and toluene (30 ml) is prepared and to this is added, dropwise, 4-chlorophenyl isocyanate (1.40 g, 0.009 mol) dissolved in toluene (20 ml). The reaction mixture is maintained under reflux for 10 h and then washed with 3×10 ml of 10% strength aqueous hydrochloric acid and 3×10 ml of water, dried over sodium sulphate and filtered. After concentrating the filtrate by evaporation, the residue is dissolved in methylene chloride and reprecipitated from petroleum ether. 2.09 (75% of theoretical) of 5-(4-chlorophenyl)-4,6-dioxo-1,5-diazabicyclo-[4.4.0]-decane with a melting point of 139°–141° C. are obtained.

Example 2

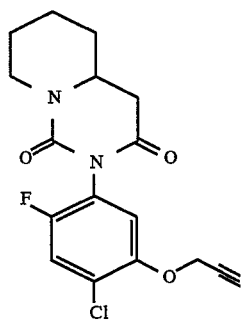

A mixture of 5-(4-chloro-2-fluoro-5-hydroxyphenyl)-4,6,-dioxo-1,5-diazabi cyclo-[4.4.0]-decane (3.13 g, 0.01 mol), potassium carbonate (6.95 g, 0.05 mol), propargyl bromide (1.78 g, 12.0 mmol) and acetonitrile (60 ml) is stirred for 72 hours at room temperature. The reaction mixture is acidified to pH 2 with 5% strength aqueous hydrochloric acid and then extracted with 3×15 ml of ether. The ethereal layer is dried over sodium sulphate and then filtered. After evaporating off the solvent, the residue is purified using silica gel chromatography.

3.11 g (89% of theoretical) of 5-(4-chloro-2-fluoro-5-propargyloxyphenyl)-4,6-dioxo-1,5-dia zabicyclo-[4.4.0]-decane are obtained as a colourless oil.

The compounds of the general formula I listed in the following Tables can be prepared, by analogy with examples 1 and 2, in accordance with the general description of methods A to D according to the present invention.

TABLE 1(A)

| $R^1$ | $R^2$ | $R^3$ | $R^4$ | $R^5$ | $R^6$ | $R^7$ | m | X | melting point °C. |
|---|---|---|---|---|---|---|---|---|---|
| H | H | H | H | H | Cl | H | 2 | $CH_2$ | 139–141 |
| H | H | H | H |   | Cl | H | 2 | $CH_2$ |  |
| H | H | H | H | F | Cl | $CO_2CH(CH_3)_2$ | 2 | $CH_2$ | oil |
| H | H | H | H | F | Cl | $CO_2CH_3$ | 2 | $CH_2$ |  |
| H | H | H | H | F | Cl | $CO_2C_2H_5$ | 2 | $CH_2$ |  |
| H | H | H | H | F | Cl | $CO_2CH(CH_3)CF_3$ | 2 | $CH_2$ |  |
| H | H | H | H | F | Cl | $CO_2CH_2CH_2CH_3$ | 2 | $CH_2$ |  |
| H | H | H | H | F | Cl | $CO_2CH(CH_3)CH_2CH_3$ | 2 | $CH_2$ | resin |
| H | H | H | H | F | Cl | $CO_2CH_2CH(CH_3)_2$ | 2 | $CH_2$ |  |
| H | H | H | H | F | Cl | $CO_2CH_2C\equiv CH$ | 2 | $CH_2$ |  |
| H | H | H | H | F | Cl | $CO_2CH(CH_3)C\equiv CH$ | 2 | $CH_2$ |  |
| H | H | H | H | F | Cl | $CO_2CH_2CF_3$ | 2 | $CH_2$ |  |
| H | H | H | H | F | Cl | $CO_2N(CH_3)_2$ | 2 | $CH_2$ |  |
| H | H | H | H | F | Cl | $CO_2CH(CH_3)CO_2C_2H_5$ | 2 | $CH_2$ |  |
| H | H | H | H | F | Cl | $OCH_3$ | 2 | $CH_2$ |  |
| H | H | H | H | F | Cl | $OCH(CH_3)_2$ | 2 | $CH_2$ | oil |
| H | H | H | H | F | Cl | $OCH_2C\equiv CH$ | 2 | $CH_2$ | oil |
| H | H | H | H | F | Cl | $OCH(CH_3)C\equiv CH$ | 2 | $CH_2$ | oil |
| H | H | H | H | F | Cl | $OCH_2C(O)N(CH_3)_2$ | 2 | $CH_2$ |  |
| H | H | H | H | F | Cl | $OCH_2P(O)(OC_2H_5)_2$ | 2 | $CH_2$ |  |
| H | H | H | H | F | Cl | $OCH_2P(S)(OC_2H_5)_2$ | 2 | $CH_2$ |  |
| H | H | H | H | F | Cl | $OCF_2CHFCl$ | 2 | $CH_2$ |  |
| H | H | H | H | F | Cl | $OCHF_2$ | 2 | $CH_2$ |  |
| H | H | H | H | F | Cl | $OCH_2CH=CH_2$ | 2 | $CH_2$ | resin |
| H | H | H | H | F | Cl | $OCH_2CH=CHCl$ | 2 | $CH_2$ |  |
| H | H | H | H | F | Cl | $OCH_2C(Cl)=CH_2$ | 2 | $CH_2$ |  |
| H | H | H | H | F | Cl | $SCH_2CO_2H$ | 2 | $CH_2$ |  |
| H | H | H | H | F | Cl | $SCH_2CO_2CH_3$ | 2 | $CH_2$ |  |
| H | H | H | H | F | Cl | $NHSO_2CH_3$ | 2 | $CH_2$ |  |
| H | H | H | H | F | Cl | $NHSO_2CH_2CH_3$ | 2 | $CH_2$ |  |
| H | H | H | H | F | Cl | $NHSO_2CF_3$ | 2 | $CH_2$ |  |
| H | H | H | H | F | Cl | $NHSO_2CH(CH_3)_2$ | 2 | $CH_2$ |  |
| H | H | H | H | F | Cl | $NHSO_2NHCH_3$ | 2 | $CH_2$ |  |

TABLE 1(A)-continued

| $R^1$ | $R^2$ | $R^3$ | $R^4$ | $R^5$ | $R^6$ | $R^7$ | m | X | melting point °C. |
|---|---|---|---|---|---|---|---|---|---|
| H | H | H | H | H | Cl | H | 2 | O |  |
| H | H | H | H |   | Cl | H | 2 | O |  |
| H | H | H | H | F | Cl | $CO_2CH(CH_3)_2$ | 2 | O | oil |
| H | H | H | H | F | Cl | $CO_2CH_3$ | 2 | O |  |
| H | H | H | H | F | Cl | $CO_2C_2H_5$ | 2 | O |  |
| H | H | H | H | F | Cl | $CO_2CH(CH_3)CF_3$ | 2 | O |  |
| H | H | H | H | F | Cl | $CO_2CH_2CH_2CH_3$ | 2 | O |  |
| H | H | H | H | F | Cl | $CO_2CH(CH_3)CH_2CH_3$ | 2 | O |  |
| H | H | H | H | F | Cl | $CO_2CH_2CH(CH_3)_2$ | 2 | O |  |
| H | H | H | H | F | Cl | $CO_2CH_2C\equiv CH$ | 2 | O |  |
| H | H | H | H | F | Cl | $CO_2CH(CH_3)C\equiv CH$ | 2 | O |  |
| H | H | H | H | F | Cl | $CO_2CH_2CF_3$ | 2 | O |  |
| H | H | H | H | F | Cl | $CO_2N(CH_3)_2$ | 2 | O |  |
| H | H | H | H | F | Cl | $CO_2CH(CH_3)CO_2C_2H_5$ | 2 | O |  |
| H | H | H | H | F | Cl | $OCH_3$ | 2 | O |  |
| H | H | H | H | F | Cl | $OCH(CH_3)_2$ | 2 | O | 127–129 |
| H | H | H | H | F | Cl | $OCH_2C\equiv CH$ | 2 | O | resin |
| H | H | H | H | F | Cl | $OCH(CH_3)C\equiv CH$ | 2 | O | oil |
| H | H | H | H | F | Cl | $OCH_2C(O)N(CH_3)_2$ | 2 | O |  |
| H | H | H | H | F | Cl | $OCH_2P(O)(OC_2H_5)_2$ | 2 | O |  |
| H | H | H | H | F | Cl | $OCH_2P(S)(OC_2H_5)_2$ | 2 | O |  |
| H | H | H | H | F | Cl | $OCF_2CHFCl$ | 2 | O |  |
| H | H | H | H | F | Cl | $OCHF_2$ | 2 | O |  |
| H | H | H | H | F | Cl | $OCH_2C=CH_2$ | 2 | O |  |
| H | H | H | H | F | Cl | $OCH_2CH=CHCl$ | 2 | O |  |
| H | H | H | H | F | Cl | $OCH_2C(Cl)=CH_2$ | 2 | O |  |
| H | H | H | H | F | Cl | $SCH_2CO_2H$ | 2 | O |  |
| H | H | H | H | F | Cl | $SCH_2CO_2CH_3$ | 2 | O |  |
| H | H | H | H | F | Cl | $NHSO_2CH_3$ | 2 | O |  |
| H | H | H | H | F | Cl | $NHSO_2CF_3$ | 2 | O |  |

TABLE 1(B)

| R¹ | R² | R³ | R⁴ | R⁵ | R⁶ | R⁷ | m | X | melting point °C. |
|---|---|---|---|---|---|---|---|---|---|
| H | H | H | H | H | Cl | H | 2 | CH₂ | 139–141 |
| H | H | H | H | F | Cl | H | 2 | CH₂ | |
| H | H | H | H | F | Cl | CO₂CH(CH₃)₂ | 2 | CH₂ | oil |
| H | H | H | H | F | Cl | CO₂CH₃ | 2 | CH₂ | |
| H | H | H | H | F | Cl | CO₂C₂H₅ | 2 | CH₂ | |
| H | H | H | H | F | Cl | CO₂CH(CH₃)CF₃ | 2 | CH₂ | |
| H | H | H | H | F | Cl | CO₂CH₂CH₂CH₃ | 2 | CH₂ | |
| H | H | H | H | F | Cl | CO₂CH(CH₃)CH₂CH₃ | 2 | CH₂ | resin |
| H | H | H | H | F | Cl | CO₂CH₂C≡CH | 2 | CH₂ | |
| H | H | H | H | F | Cl | CO₂CH(CH₃)C≡CH | 2 | CH₂ | |
| H | H | H | H | F | Cl | CO₂CH₂CF₃ | 2 | CH₂ | |
| H | H | H | H | F | Cl | CON(CH₃)₂ | 2 | CH₂ | |
| H | H | H | H | F | Cl | CO₂CH(CH₃)CO₂C₂H₅ | 2 | CH₂ | |
| H | H | H | H | F | Cl | OCH₃ | 2 | CH₂ | |
| H | H | H | H | F | Cl | OCH(CH₃)₂ | 2 | CH₂ | oil |
| H | H | H | H | F | Cl | OCH₂C≡CH | 2 | CH₂ | oil |
| H | H | H | H | F | Cl | OCH₂P(S)(OC₂H₅)₂ | 1 | CH₂ | |
| H | H | H | H | F | Cl | OCF₂CHFCl | 1 | CH₂ | |
| H | H | H | H | F | Cl | OCHF₂ | 1 | CH₂ | |
| H | H | H | H | F | Cl | OCH₂CH=CH₂ | 1 | CH₂ | resin |
| H | H | H | H | F | Cl | OCH₂CH=CHCl | 1 | CH₂ | |
| H | H | H | H | F | Cl | OCH₂C(Cl)=CH₂ | 1 | CH₂ | |
| H | H | H | H | F | Cl | CN | 1 | CH₂ | |
| H | H | H | H | F | Cl | SCH₂CO₂H | 1 | CH₂ | |
| H | H | H | H | F | Cl | SCH(CH₃)₂ | 1 | CH₂ | |
| H | H | H | H | F | Cl | SCH₂CO₂CH₃ | 1 | CH₂ | |
| H | H | H | H | F | Cl | SCH₂C≡CH | 1 | CH₂ | |
| H | H | H | H | F | Cl | NHSO₂CH₃ | 1 | CH₂ | |
| H | H | H | H | F | Cl | NHSO₂CF₃ | 1 | CH₂ | |
| H | H | H | H | F | Cl | NHSO₂CH(CH₃)₂ | 1 | CH₂ | |
| H | H | H | H | F | Cl | NHSO₂NHCH₃ | 1 | CH₂ | |
| H | H | H | H | F | Cl | OCH₂CO₂C₅H₁₁ | 1 | CH₂ | |
| H | H | H | H | F | Cl | OCH₂CH=N—OCH₃ | 1 | CH₂ | |
| H | H | H | H | F | Cl | OCH₂C=N—OCH₂CH=CH₂ | 1 | CH₂ | |
| H | H | H | H | F | Cl | OSi(CH₃)₃ | 1 | CH₂ | |
| H | H | H | H | F | Cl | OCH₂C(O)N⟨morpholino⟩ | 1 | CH₂ | |
| H | H | H | H | Cl | Cl | CO₂CH(CH₃)₂ | 1 | CH₂ | |
| H | H | H | H | Cl | Cl | CO₂CH(CH₃)C₂H₅ | 1 | CH₂ | |
| H | H | H | H | F | Cl | CO₂CH(CH₃)CH₂CH₃ | 2 | O | |
| H | H | H | H | F | Cl | CO₂CH₂CH(CH₃)₂ | 2 | O | |
| | H | H | H | F | Cl | CO₂CH₂C≡CH | 2 | O | |
| H | H | H | H | F | Cl | CO₂CH(CH₃)C≡CH | 2 | O | |
| H | H | H | H | F | Cl | CO₂CH₂CF₃ | 2 | O | |
| H | H | H | H | F | Cl | CON(CH₃)₂ | 2 | O | |
| H | H | H | H | F | Cl | CO₂CH(CH₃)CO₂C₂H₅ | 2 | O | |
| H | H | H | H | F | Cl | OCH₃ | 2 | O | |
| H | H | H | H | F | Cl | OCH(CH₃)₂ | 2 | O | 127–129 |
| H | H | H | H | F | Cl | OCH₂C≡CH | 2 | O | resin |
| H | H | H | H | F | Cl | OCH(CH₃)C≡CH | 2 | O | oil |
| H | H | H | H | F | Cl | OCH₂C(O)N(CH₃)₂ | 2 | O | |
| H | H | H | H | F | Cl | OCH₂P(O)(OC₂H₅)₂ | 2 | O | |
| H | H | H | H | F | Cl | OCH₂P(S)(OC₂H₅)₂ | 2 | O | |
| H | H | H | H | F | Cl | OCF₂CHFCl | 2 | O | |
| H | H | H | H | F | Cl | OCHF₂ | 2 | O | |

TABLE 1(B)-continued

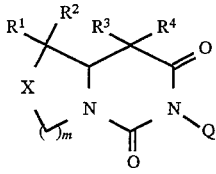

| R¹ | R² | R³ | R⁴ | R⁵ | R⁶ | R⁷ | m | X | melting point °C. |
|---|---|---|---|---|---|---|---|---|---|
| H | H | H | H | F | Cl | OCH$_2$C≡CH$_2$ | 2 | O | |
| H | H | H | H | F | Cl | OCH$_2$CH≡CHCl | 2 | O | |
| H | H | H | H | F | Cl | OCH$_2$C(Cl)=CH$_2$ | 2 | O | |
| H | H | H | H | F | Cl | SCH$_2$CO$_2$H | 2 | O | |
| H | H | H | H | F | Cl | SCH$_2$CO$_2$CH$_3$ | 2 | O | |
| H | H | H | H | F | Cl | NHSO$_2$CH$_3$ | 2 | O | |
| H | H | H | H | F | Cl | NHSO$_2$CF$_3$ | 2 | O | |
| H | H | H | H | F | Cl | NHSO$_2$CH(CH$_3$)$_2$ | 2 | O | |
| H | H | H | H | F | Cl | NHSO$_2$NHCH$_3$ | 2 | O | |
| H | H | H | H | H | Cl | H | 1 | CH$_2$ | |
| H | H | H | H | F | Cl | H | 1 | CH$_2$ | |
| H | H | H | H | F | Cl | CO$_2$CH(CH$_3$)$_2$ | 1 | CH$_2$ | oil |
| H | H | H | H | F | Cl | CO$_2$CH$_3$ | 1 | CH$_2$ | oil |
| H | H | H | H | F | Cl | CO$_2$C$_2$H$_5$ | 1 | CH$_2$ | oil |
| H | H | H | H | F | Cl | CO$_2$CH(CH$_3$)CF$_3$ | 1 | CH$_2$ | resin |
| H | H | H | H | F | Cl | CO$_2$CH$_2$CH$_2$CH$_3$ | 1 | CH$_2$ | oil |
| H | H | H | H | F | Cl | CO$_2$CH(CH$_3$)CH$_2$CH$_3$ | 1 | CH$_2$ | oil |
| H | H | H | H | F | Cl | CO$_2$CH$_2$CH(CH$_3$)$_2$ | 1 | CH$_2$ | oil |
| H | H | H | H | F | Cl | CO$_2$CH$_2$C≡CH | 1 | CH$_2$ | |
| H | H | H | H | F | Cl | CO$_2$CH(CH$_3$)C≡CH | 1 | CH$_2$ | resin |
| H | H | H | H | F | Cl | CO$_2$CH$_2$CF$_3$ | 1 | CH$_2$ | |
| H | H | H | H | F | Cl | CON(CH$_3$)$_2$ | 1 | CH$_2$ | |
| H | H | H | H | F | Cl | CO$_2$CH(CH$_3$)CO$_2$C$_2$H$_5$ | 1 | CH$_2$ | |
| H | H | H | H | F | Cl | OCH$_3$ | 1 | CH$_2$ | |
| H | H | H | H | F | Cl | OCH(CH$_3$)$_2$ | 1 | CH$_2$ | oil |
| H | H | H | H | F | Cl | OCH$_2$C≡CH | 1 | CH$_2$ | resin |
| H | H | H | H | F | Cl | OCH(CH$_3$)C≡CH | 1 | CH$_2$ | resin |
| H | H | H | H | F | Cl | OCH(CH$_3$)CH$_2$CH$_3$ | 1 | CH$_2$ | resin |
| H | H | H | H | F | Cl | OCH$_2$C(O)N(CH$_3$)$_2$ | 1 | CH$_2$ | |
| H | H | H | H | F | Cl | OCH$_2$P(O)(OC$_2$H$_5$)$_2$ | 1 | CH$_2$ | |
| H | H | H | H | F | Cl | OCH$_2$P(S)(OC$_2$H$_5$)$_2$ | 1 | CH$_2$ | |
| H | H | H | H | F | Cl | OCF$_2$CHFCl | 1 | CH$_2$ | |
| H | H | H | H | F | Cl | OCHF$_2$ | 1 | CH$_2$ | |
| H | H | H | H | F | Cl | OCH$_2$CH=CH$_2$ | 1 | CH$_2$ | resin |
| H | H | H | H | F | Cl | OCH$_2$CH=CHCl | 1 | CH$_2$ | |
| H | H | H | H | F | Cl | OCH$_2$C(Cl)=CH$_2$ | 1 | CH$_2$ | |
| H | H | H | H | F | Cl | CN | 1 | CH$_2$ | |
| H | H | H | H | F | Cl | SCH$_2$CO$_2$H | 1 | CH$_2$ | |
| H | H | H | H | F | Cl | SCH(CH$_3$)$_2$ | 1 | CH$_2$ | |
| H | H | H | H | F | Cl | SCH$_2$CO$_2$CH$_3$ | 1 | CH$_2$ | |
| H | H | H | H | F | Cl | SCH$_2$C≡CH | 1 | CH$_2$ | |
| H | H | H | H | F | Cl | NHSO$_2$CH$_3$ | 1 | CH$_2$ | |
| H | H | H | H | F | Cl | NHSO$_2$CF$_3$ | 1 | CH$_2$ | |
| H | H | H | H | F | Cl | NHSO$_2$CH(CH$_3$)$_2$ | 1 | CH$_2$ | |
| H | H | H | H | F | Cl | NHSO$_2$NHCH$_3$ | 1 | CH$_2$ | |
| H | H | H | H | F | Cl | OCH$_2$CO$_2$C$_5$H$_{11}$ | 1 | CH$_2$ | |
| H | H | H | H | F | Cl | OSi(CH$_3$)$_3$ | 1 | CH$_2$ | |
| H | H | H | H | F | Cl | OCH$_2$C(O)N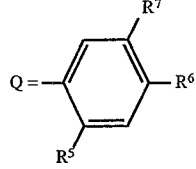O | 1 | CH$_2$ | |
| H | H | H | H | Cl | Cl | CO$_2$CH(CH$_3$)$_2$ | 1 | CH$_2$ | |
| H | H | H | H | Cl | Cl | CO$_2$CH(CH$_3$)C$_2$H$_5$ | 1 | CH$_2$ | |
| H | H | H | H | F | Cl | CO$_2$CH(CH$_3$)$_2$ | 1 | CHOCHF$_2$ | |
| H | H | H | H | F | Cl | CO$_2$CH(CH)$_3$CH$_2$CH$_3$ | 1 | CHOCHF$_2$ | |
| H | H | H | H | F | Cl | OCH$_3$ | 1 | CHOCHF$_2$ | |
| H | H | H | H | F | Cl | OCH(CH$_3$)$_2$ | 1 | CHOCHF$_2$ | |
| H | H | H | H | F | Cl | OCH$_2$C≡CH | 1 | CHOCHF$_2$ | |

TABLE 1(B)-continued

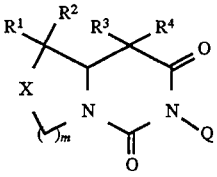

| R¹ | R² | R³ | R⁴ | R⁵ | R⁶ | R⁷ | m | X | melting point °C. |
|---|---|---|---|---|---|---|---|---|---|
| H | H | H | H | F | Cl | OCH(CH₃)C≡CH | 1 | CHOCHF₂ | |
| H | H | H | H | F | Cl | OCH₂C≡CH₂ | 1 | CHOCHF₂ | |
| H | H | H | H | F | Cl | CO₂CH(CH₃)₂ | 1 | CHOCF₃ | |
| H | H | H | H | F | Cl | CO₂CH(CH₃)CH₂CH₃ | 1 | CHOCF₃ | |
| H | H | H | H | F | Cl | OCH₃ | 1 | CHOCF₃ | |
| H | H | H | H | F | Cl | OCH(CH₃)₂ | 1 | CHOCF₃ | |
| H | H | H | H | F | Cl | OCH₂C≡CH | 1 | CHOCF₃ | |
| H | H | H | H | F | Cl | OCH(CH₃)C≡CH— | 1 | CHOCF₃ | |
| H | H | H | H | F | Cl | OCH₂C=CH₂ | 1 | CHOCF₃ | |
| H | H | H | H | F | Cl | CO₂CH(CH₃)₂ | 1 | CHOCH₂CF₃ | |
| H | H | H | H | F | Cl | CO₂CH(CH₃)CH₂CH₃ | 1 | CHOCH₂CF₃ | |
| H | H | H | H | F | Cl | OCH₃ | 1 | CHOCH₂CF₃ | |
| H | H | H | H | F | Cl | OCH(CH₃)₂ | 1 | CHOCH₂CF₃ | |
| H | H | H | H | F | Cl | OCH₂C≡CH | 1 | CHOCH₂CF₃ | |
| H | H | H | H | F | Cl | OCH(CH₃)C≡CH | 1 | CHOCH₂CF₃ | |
| H | H | H | H | F | Cl | OCH₂C=CH₂ | 1 | CHOCH₂CF₃ | |
| H | H | H | (CH₂)₃Br | F | Cl | CO₂CH(CH₃)₂ | 2 | CH₂ | |
| H | H | H | H | F | Cl | CO₂CH(CH₃)₂ | 2 | CF₂ | |
| H | H | H | H | F | Cl | CO₂CH(CH₃)₂ | 1 | CF₂ | |
| H | H | H | H | F | Cl | OCH(CH₃)₂ | 1 | CF₂ | |
| H | H | H | H | F | Cl | OCH₂C≡CH | 1 | CF₂ | |
| H | H | H | H | F | Cl | OCH(CH₃)C≡CH | 1 | CF₂ | |
| H | H | H | H | F | Cl | SCH₂CO₂CH₃ | 1 | CF₂ | |
| H | H | H | H | F | Cl | OCH₂CH₂CH₃ | 1 | CF₂ | |
| H | H | H | H | F | Cl | CO₂CH₃ | 1 | CF₂ | |
| H | H | H | H | F | Cl | CO₂CH₂CH₃ | 1 | CF₂ | |
| H | H | H | H | Cl | Cl | CO₂CH(CH₃)₂ | 1 | CF₂ | |
| H | H | H | H | Cl | Cl | OCH₂C≡CH | 1 | CF₂ | |
| H | H | H | H | Cl | Cl | OCH(CH₃)C≡CH | 1 | CF₂ | |

TABLE 2

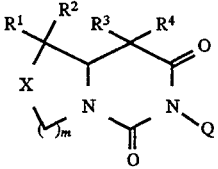

| R¹ | R² | R³ | R⁴ | R⁵ | R⁶ | R⁸ | R⁹ | m | X | W | melting point °C. |
|---|---|---|---|---|---|---|---|---|---|---|---|
| H | H | H | H | F | Cl | H | H | 2 | CH₂ | O | |
| H | H | H | H | F | Cl | H | CH₃ | 2 | CH₂ | O | |
| H | H | H | H | F | Cl | H | CH₂F | 2 | CH₂ | O | |
| H | H | H | H | F | Cl | CH₃ | CH₃ | 2 | CH₂ | O | |
| H | H | H | H | F | Cl | H | CH₃ | 2 | O | O | |
| H | H | H | H | F | Cl | H | CH₃ | 2 | S | O | |
| H | H | H | H | F | Cl | H | CH₃ | 1 | CH₂ | O | |
| H | H | H | H | F | Cl | CH₃ | CH₃ | 1 | CH₂ | O | |
| H | H | H | H | F | Cl | H | CH₂F | 1 | CH₂ | O | |
| H | H | H | H | F | Cl | H | CH₂Cl | 1 | CH₂ | O | |

TABLE 2-continued

| R¹ | R² | R³ | R⁴ | R⁵ | R⁶ | R⁸ | R⁹ | m | X | W | melting point °C. |
|---|---|---|---|---|---|---|---|---|---|---|---|
| H | H | H | H | F | Cl | H | CH₂Br | 1 | CH₂ | O | |
| H | H | H | H | F | Cl | H | CH(CH₃)₂ | 1 | CH₂ | O | |
| H | H | H | H | F | Cl | H | CH₂CH₃ | 1 | CH₂ | O | |
| H | H | H | H | F | Br | H | CH₃ | 1 | CH₂ | O | |
| H | H | H | H | F | OCH₃ | H | CH₃ | 1 | CH₂ | O | |
| H | H | H | H | F | CH₃ | H | CH₃ | 1 | CH₂ | O | |
| H | H | H | H | F | CN | H | CH₃ | 1 | CH₂ | O | |
| H | H | H | H | F | CF₃ | H | CH₃ | 1 | CH₂ | O | |
| H | H | H | H | F | OCHF₂ | H | CH₃ | 1 | CH₂ | O | |
| H | H | H | H | F | Cl | H | CH₃ | 2 | CH₂ | S | |
| H | H | H | H | F | Cl | H | CH₃ | 1 | CH₂ | S | |
| H | H | H | H | F | Cl | H | CH₃ | 2 | O | S | |
| H | H | H | H | F | Cl | H | CH₃ | 1 | CHF | O | 145–147 (1 isomer) |
| H | H | H | H | F | Cl | H | CH₃ | 1 | CHCl | O | |
| H | H | H | H | F | Cl | H | CH₃ | 1 | CHF | S | |
| H | H | H | H | F | Cl | H | CH₃ | 1 | CHCl | S | |
| H | H | H | CH₃ | F | Cl | H | CH₃ | 1 | CH₂ | O | |
| H | H | CH₃ | CH₃ | F | Cl | H | CH₃ | 1 | CH₂ | O | |
| H | H | H | C₆H₅ | F | Cl | H | CH₃ | 1 | CH₂ | O | |
| H | H | H | H | F | Cl | H | CH₃ | 1 | CHBr | O | |
| H | H | H | H | F | Cl | H | CH₃ | 1 | CHOCHF₂ | O | |
| H | H | H | H | F | Cl | H | CH₃ | 1 | CHOCF₃ | O | |
| H | H | H | H | F | Cl | H | CH₃ | 1 | CHOCH₂CF₃ | O | |
| H | H | H | H | F | Cl | H | CH₃ | 2 | CF₂ | O | |
| H | H | H | H | F | Cl | H | CH₃ | 1 | CF₂ | O | |
| H | H | H | H | Cl | Cl | H | CH₃ | 1 | CF₂ | O | |

TABLE 3

| R¹ | R² | R³ | R⁴ | R⁵ | R⁶ | R⁸ | R⁹ | m | X | w | melting point °C. |
|---|---|---|---|---|---|---|---|---|---|---|---|
| H | H | H | H | F | Cl | H | Cl | 2 | CH₂ | S | |
| H | H | H | H | F | Cl | H | H | 2 | CH₂ | S | |
| H | H | H | H | F | Cl | H | CH₃ | 2 | CH₂ | S | |
| H | H | H | H | F | Cl | CH₃ | CH₃ | 2 | CH₂ | S | |
| H | H | H | H | H | SCH₃ | H | H | 2 | CH₂ | S | |
| H | H | H | H | F | Cl | H | Cl | 2 | O | S | |
| H | H | H | H | F | Cl | H | CH₃ | 2 | O | S | |
| H | H | H | H | F | Cl | H | H | 1 | CH₂ | S | |
| H | H | H | H | F | Cl | H | Cl | 1 | CH₂ | S | |
| H | H | H | H | F | Cl | H | CH₃ | 1 | CH₂ | S | |
| H | H | H | H | F | Cl | CH₃ | CH₃ | 1 | CH₂ | S | |
| H | H | H | H | H | SCH₃ | H | H | 1 | CH₂ | S | |
| H | H | H | H | F | Cl | H | Cl | 1 | CHCl | S | |
| H | H | H | H | F | Cl | H | Cl | 1 | CHF | S | |
| H | H | H | H | F | Cl | H | CH₃ | 1 | CHCl | S | |
| H | H | H | H | F | Cl | H | CH₃ | 1 | CHF | S | |
| H | H | H | H | F | Cl | H | Cl | 1 | CH₂ | O | |
| H | H | H | H | F | Cl | H | H | 1 | CH₂ | O | |

TABLE 3-continued

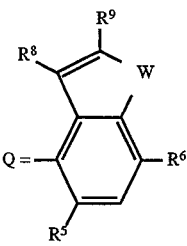

| R¹ | R² | R³ | R⁴ | R⁵ | R⁶ | R⁸ | R⁹ | m | X | w | melting point °C. |
|---|---|---|---|---|---|---|---|---|---|---|---|
| H | H | H | H | F | Cl | H | CH₃ | 1 | CH₂ | O | |
| H | H | H | CH₃ | F | Cl | H | H | 1 | CH₂ | S | |
| H | H | CH₃ | CH₃ | F | Cl | H | H | 1 | CH₂ | S | |
| H | H | H | C₆H₅ | F | Cl | H | H | 1 | CH₂ | S | |
| H | H | H | H | F | Cl | H | C₂H₅ | 1 | CH₂ | S | |
| H | H | H | H | F | Cl | H | Cl | 1 | CHBr | S | |
| H | H | H | H | F | Cl | H | CH₃ | 1 | CHBr | S | |
| H | H | H | H | F | Cl | H | Cl | 1 | CHOCHF₂ | S | |
| H | H | H | H | F | Cl | H | CH₃ | 1 | CHOCHF₂ | S | |
| H | H | H | H | F | Cl | H | Cl | 1 | CHOCF₃ | S | |
| H | H | H | H | F | Cl | H | CH₃ | 1 | CHOCF₃ | S | |
| H | H | H | H | F | Cl | H | Cl | 1 | CHOCH₂CF₃ | S | |
| H | H | H | H | F | Cl | H | Cl | 2 | CF₂ | S | |
| H | H | H | H | F | Cl | H | Cl | 1 | CF₂ | S | |
| H | H | H | H | Cl | Cl | H | Cl | 1 | CF₂ | S | |

TABLE 4

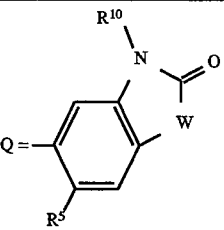

| R¹ | R² | R³ | R⁴ | R⁵ | R¹⁰ | m | X | w | melting point °C. |
|---|---|---|---|---|---|---|---|---|---|
| H | H | H | H | F | H | 2 | CH₂ | S | |
| H | H | H | H | F | CH₃ | 2 | CH₂ | S | |
| H | H | H | H | F | CH₂C≡CH | 2 | CH₂ | S | |
| H | H | H | H | F | CH₂CH=CH₂ | 2 | CH₂ | S | |
| H | H | H | H | F | CH₂C≡CH | 2 | O | S | |
| H | H | H | H | F | CH₂C=CH₂ | 2 | O | S | |
| H | H | H | H | F | H | 1 | CH₂ | S | |
| H | H | H | H | F | CH₃ | 1 | CH₂ | S | |
| H | H | H | H | F | CH₂C≡CH | 1 | CH₂ | S | |
| H | H | H | H | F | CH(CH₃)C≡CH | 1 | CH₂ | S | |
| H | H | H | H | F | CH₂C=CH₂ | 1 | CH₂ | S | |
| H | H | H | H | F | CH₂OCH₃ | 1 | CH₂ | S | |
| H | H | H | H | F | CH(CH₃)₂ | 1 | CH₂ | S | |
| H | H | H | H | F | CHF₂ | 1 | CH₂ | S | |
| H | H | H | H | F | CF₂CHF₂ | 1 | CH₂ | S | |
| H | H | H | H | F | CH₂CH=CHCH₃ | 1 | CH₂ | S | |
| H | H | H | H | F | CH₂CH₂CH₃ | 1 | CH₂ | S | |
| H | H | H | H | F | CH₂C≡CH | 1 | CH₂ | O | |
| H | H | H | H | F | CH₂CH=CH₂ | 1 | CH₂ | O | |
| H | H | H | H | Cl | CH₂C=CH | 1 | CH₂ | S | |
| H | H | H | H | F | CH₂C≡CH | 1 | CHF | S | |
| H | H | H | H | F | CH₂CH=CH₂ | 1 | CHF | S | |
| H | H | H | H | F | CH₂C=CH | 1 | CHCl | S | |
| H | H | H | H | F | CH₂CH=CH₂ | 1 | CHCl | S | |
| H | H | H | H | F | CH₃ | 1 | CHCl | S | |

TABLE 4-continued

| R¹ | R² | R³ | R⁴ | R⁵ | R¹⁰ | m | X | w | melting point °C. |
|---|---|---|---|---|---|---|---|---|---|
| H | H | H | CH₃ | F | CH₂C≡CH | 1 | CH₂ | S | |
| H | H | CH₃ | CH₃ | F | CH₂C≡CH | 1 | CH₂ | S | |
| H | H | H | H | H | CH₂C≡CH | 1 | CH₂ | S | |
| H | H | H | H | F | CH₂C≡CH | 1 | CHBr | S | |
| H | H | H | H | F | CH₂CH=CH₂ | 1 | CHBr | S | |
| H | H | H | H | F | CH₂C≡CH | 1 | CHBr | O | |
| H | H | H | H | F | CH₂C≡CH | 1 | CHOCHF₂ | S | |
| H | H | H | H | F | CH₂C≡CH | 1 | CHOCF₃ | S | |
| H | H | H | H | F | CH₂C≡CH | 1 | CHOCH₂CF₃ | S | |
| H | H | H | H | F | CH₂C≡CH | 1 | CF₂ | S | |
| H | H | H | H | F | CH₂C≡CH | 2 | CF₂ | S | |

TABLE 5

| R¹ | R² | R³ | R⁴ | R⁵ | R⁸ | R⁹ | R¹⁰ | m | X | w | melting point °C. |
|---|---|---|---|---|---|---|---|---|---|---|---|
| H | H | H | H | F | H | H | CH₃ | 2 | CH₂ | O | |
| H | H | H | H | F | H | H | C₂H₅ | 2 | CH₂ | O | |
| H | H | H | H | F | H | H | CH₂C≡CH | 2 | CH₂ | O | |
| H | H | H | H | F | H | H | CH(CH₃)C≡CH | 2 | CH₂ | O | |
| H | H | H | H | F | H | H | CH₂CH=CH₂ | 2 | CH₂ | O | |
| H | H | H | H | F | H | CH₃ | CH₂C≡CH | 2 | CH₂ | O | |
| H | H | H | H | F | H | H | CH₂C≡CH | 2 | O | O | resin |
| H | H | H | H | F | H | H | CH₂CH=CH₂ | 2 | O | O | |
| H | H | H | H | F | H | H | CH₃ | 2 | O | O | |
| H | H | H | H | H | H | H | CH₃ | 1 | CH₂ | O | |
| H | H | H | H | H | H | H | CH₂C≡CH | 1 | CH₂ | O | |
| H | H | H | H | F | H | H | CH₃ | 1 | CH₂ | O | |
| H | H | H | H | F | H | H | C₂H₅ | 1 | CH₂ | O | |
| H | H | H | H | F | H | H | CH(CH₃)₂ | 1 | CH₂ | O | |
| H | H | H | H | F | H | H | CH₂C≡CH | 1 | CF₂ | O | |
| H | H | H | H | F | H | H | CH₂C≡CH | 2 | CF₂ | O | |
| H | H | H | H | F | H | H | CH₂CH=CH₂ | 1 | CF₂ | O | |
| H | H | H | H | F | H | H | CH(CH₃)CO₂CH₃ | | CF₂ | O | |
| H | H | H | H | F | H | H | CH₂CH₂CH₃ | 1 | CH₂ | O | |
| H | H | H | H | F | H | H | CH₂CH=CH₂ | 1 | CH₂ | O | |

TABLE 5-continued

| R¹ | R² | R³ | R⁴ | R⁵ | R⁸ | R⁹ | R¹⁰ | m | X | w | melting point °C. |
|---|---|---|---|---|---|---|---|---|---|---|---|
| H | H | H | H | F | H | H | $CH_2C\equiv CH$ | 1 | $CH_2$ | O | resin |
| H | H | H | H | F | H | H | $CH(CH_3)C\equiv CH$ | 1 | $CH_2$ | O | |
| H | H | H | H | H | H | H | $CH_2C\equiv CH$ | 1 | $CH_2$ | S | |
| H | H | H | H | F | H | H | $CH_2C\equiv CH$ | 1 | $CH_2$ | S | |
| H | H | H | $CH_3$ | F | H | H | $CH_2C\equiv CH$ | 1 | $CH_2$ | O | |
| H | H | $CH_3$ | $CH_3$ | F | H | H | $CH_2C\equiv CH$ | 1 | $CH_2$ | O | |
| H | H | H | H | Cl | H | H | $CH_2C\equiv CH$ | 1 | $CH_2$ | O | |
| H | H | H | H | F | H | $CH_3$ | $CH_2C\equiv CH$ | 1 | $CH_2$ | O | |
| H | H | H | H | H | H | H | $CH_2C\equiv CH$ | 1 | CHF | O | |
| H | H | H | H | F | H | H | $CH_3$ | 1 | CHF | O | |
| H | H | H | H | F | H | H | $CH_2C\equiv CH$ | 1 | CHF | O | resin |
| H | H | H | H | F | H | H | $CH_2CH=CH_2$ | 1 | CHF | O | |
| H | H | H | H | H | H | H | $CH_2C\equiv CH$ | 1 | CHCl | O | |
| H | H | H | H | F | H | H | $CH_3$ | 1 | CHCl | O | |
| H | H | H | H | F | H | H | $CH_2C\equiv CH$ | 1 | CHCl | O | |
| H | H | H | H | F | H | H | $CH_2CH=CH_2$ | 1 | CHCl | S | |
| H | H | H | H | F | H | H | $CH_2C\equiv CH$ | 1 | CHBr | O | |
| H | H | H | H | F | H | H | $CH_2C\equiv CH$ | 1 | CHBr | S | |
| H | H | H | H | F | H | H | $CH_2CH=CH_2$ | 1 | CHBr | O | |
| H | H | H | H | F | H | H | $CH_2C\equiv CH$ | 1 | $CHOCHF_2$ | O | |
| H | H | H | H | F | H | H | $CH_2C\equiv CH$ | 1 | $CHOCF_3$ | O | |
| H | H | H | H | F | H | H | $CH_2C\equiv CH$ | 1 | $CHOCH_2CF_3$ | O | |

TABLE 6

| R¹ | R² | R³ | R⁴ | R⁵ | R⁸ | R⁹ | m | X | melting point °C. |
|---|---|---|---|---|---|---|---|---|---|
| H | H | H | H | H | F | F | 2 | $CH_2$ | |
| H | H | H | H | F | F | F | 2 | $CH_2$ | |
| H | H | H | H | F | H | H | 2 | $CH_2$ | |
| H | H | H | H | H | F | F | 2 | O | |
| H | H | H | H | F | F | F | 2 | O | |
| H | H | H | H | F | H | H | 2 | O | |
| H | H | H | H | H | F | F | 1 | $CH_2$ | |
| H | H | H | H | F | F | F | 1 | $CH_2$ | |
| H | H | H | H | F | H | H | 1 | $CH_2$ | |
| H | H | H | H | F | F | F | 1 | CHF | |
| H | H | H | H | F | F | F | 1 | CHF | |
| H | H | H | H | F | H | H | 1 | CHF | |
| H | H | H | H | F | F | F | 1 | CHCl | |
| H | H | H | H | F | F | F | 1 | CHCl | |
| H | H | H | H | F | H | H | 1 | CHCl | |
| H | H | H | $CH_3$ | F | F | F | 1 | $CH_2$ | |

TABLE 6-continued

[Structure: R¹R²C(X(CH₂)ₘ)-C(R³R⁴)-C(=O)-N(Q)-N-C(=O) ring; Q = phenyl with R⁵ and OC(R⁸)(R⁹)O dioxole substituents]

| R¹ | R² | R³ | R⁴ | R⁵ | R⁸ | R⁹ | m | X | melting point °C. |
|----|----|----|----|----|----|----|----|----|----|
| H | H | CH₃ | CH₃ | F | F | F | 1 | CH₂ | |
| H | H | H | H | F | H | H | 1 | CF₂ | |
| H | H | H | H | H | F | F | 1 | CF₂ | |
| H | H | H | H | F | F | F | 1 | CF₂ | |
| H | H | H | CH₃ | F | H | H | 1 | CH₂ | |
| H | H | CH₃ | CH₃ | F | H | H | 1 | CH₂ | |
| H | H | H | H | H | F | F | 1 | CHBr | |
| H | H | H | H | F | F | F | 1 | CHBr | |
| H | H | H | H | F | H | H | 1 | CHBr | |
| H | H | H | H | F | F | F | 1 | CHOCHF₂ | |
| H | H | H | H | F | F | F | 1 | CHOCF₃ | |
| H | H | H | H | F | F | F | 1 | CHOCH₂CF₃ | |

TABLE 7

[Structure: R¹R²C(X(CH₂)ₘ)-C(R³R⁴)-C(=O)-N(Q)-N-C(=O) ring; Q = phenyl with R⁵, R⁶ and OCH(R⁷)CH(R⁸)O- type dioxolane substituents]

| R¹ | R² | R³ | R⁴ | R⁵ | R⁶ | R⁷ | R⁸ | m | X | melting point °C. |
|----|----|----|----|----|----|----|----|----|----|----|
| H | H | H | H | H | H | CO₂CH₃ | H | 2 | CH₂ | |
| H | H | H | H | H | H | CO₂CH₃ | CH₃ | 2 | CH₂ | |
| H | H | H | H | H | H | CO₂CH₃ | CH₃ | 1 | CH₂ | |
| H | H | H | H | H | H | CO₂C₂H₅ | CH₃ | 1 | CH₂ | |
| H | H | H | H | H | H | CO₂C₂H₅ | H | 1 | CH₂ | |
| H | H | H | H | H | H | CO₂(CH₂)₂CH₃ | CH₃ | 1 | CH₂ | |
| H | H | H | H | H | H | CO₂(CH₂)₂CH₃ | H | 1 | CH₂ | |
| H | H | H | H | H | H | CO₂(CH₂)₃CH₃ | CH₃ | 1 | CH₂ | |
| H | H | H | H | H | H | CO₂(CH₂)₃CH₃ | H | 1 | CH₂ | |
| H | H | H | H | H | H | CO₂CH₂C≡CH | CH₃ | 1 | CH₂ | |
| H | H | H | H | H | Cl | CO₂CH₃ | CH₃ | 1 | CH₂ | |
| H | H | H | H | H | Cl | CO₂C₂H₅ | CH₃ | 1 | CH₂ | |
| H | H | H | H | H | Cl | CO₂(CH₂)₂CH₃ | CH₃ | 1 | CH₂ | |
| H | H | H | H | H | Cl | CO₂(CH₂)₃CH₃ | CH₃ | 1 | CH₂ | |
| H | H | H | H | H | Cl | CO₂CH₂C≡CH | CH₃ | 1 | CH₂ | |
| H | H | H | H | F | Cl | CO₂CH₃ | CH₃ | 1 | CH₂ | |
| H | H | H | H | F | Cl | CO₂C₂H₅ | CH₃ | 1 | CH₂ | |
| H | H | H | H | F | Cl | CO₂(CH₂)₂CH₃ | CH₃ | 1 | CH₂ | |
| H | H | H | H | F | Cl | CO₂(CH₂)₂CH₃ | H | 1 | CH₂ | |
| H | H | H | H | F | Cl | CO₂CH₂CH≡CH | CH₃ | 1 | CH₂ | |
| H | H | H | H | F | Cl | CO₂CH(CH₃)C≡CH | CH₃ | 1 | CH₂ | |
| H | H | H | H | F | Cl | CO₂CHCH=CH₂ | CH₃ | 1 | CH₂ | |
| H | H | H | H | F | Cl | CO₂CH(CH₃)₂ | CH₃ | 1 | CHF | |
| H | H | H | H | F | Cl | CO₂(CH₂)₃CH₃ | CH₃ | 1 | CHF | |
| H | H | H | H | F | Cl | CO₂CH(CH₃)CH₂CH₃ | CH₃ | 1 | CHF | |
| H | H | H | H | F | Cl | CO₂(CH₂)₂CH₃ | CH₃ | 1 | CHF | |
| H | H | H | H | F | Cl | CO₂(CH₂)₃CH₃ | CH₃ | 1 | CHF | |

TABLE 7-continued

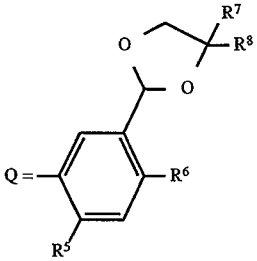

| R¹ | R² | R³ | R⁴ | R⁵ | R⁶ | R⁷ | R⁸ | m | X | melting point °C. |
|---|---|---|---|---|---|---|---|---|---|---|
| H | H | H | H | F | Cl | $CO_2CH(CH_3)_2$ | $CH_3$ | 1 | CHCl | |
| H | H | H | H | F | Cl | $CO_2(CH_2)_2CH_3$ | $CH_3$ | 1 | CHCl | |
| H | H | H | H | F | Cl | $CO_2CH_3$ | $CH_3$ | 1 | CHCl | |
| H | H | H | H | F | Cl | $CO_2CH_2CH_3$ | $CH_3$ | 1 | CHCl | |
| H | H | H | H | F | Cl | $CO_2(CH_2)_3CH_3$ | $CH_3$ | 1 | CHBr | |
| H | H | H | H | F | Cl | $CO_2(CH_2)_2CH_3$ | $CH_3$ | 1 | CHBr | |
| H | H | H | H | F | Cl | $CO_2CH_3$ | $CH_3$ | 1 | CHBr | |
| H | H | H | H | F | Cl | $CO_2CH_3$ | $CH_3$ | 1 | $CHOCHF_2$ | |
| H | H | H | H | F | Cl | $CO_2CH_2CH_3$ | $CH_3$ | 1 | $CHOCHF_2$ | |
| H | H | H | H | F | Cl | $CO_2(CH_2)_3CH_3$ | $CH_3$ | 1 | $CHOCHF_2$ | |
| H | H | H | H | F | Cl | $CO_2CH_3$ | $CH_3$ | 1 | $CHOCF_3$ | |
| H | H | H | H | F | Cl | $CO_2(CH_2)_3CH_3$ | $CH_3$ | 1 | $CHOCF_3$ | |
| H | H | H | H | F | Cl | $CO_2CH_3$ | $CH_3$ | 1 | $CHOCH_2CF_3$ | |
| H | H | H | H | F | Cl | $CO_2(CH_2)_3CH_3$ | $CH_3$ | 1 | $CHOCH_2CF_3$ | |
| H | H | H | H | H | Cl | $CO_2CH_2C\equiv CH$ | $CH_3$ | 1 | CHF | |
| H | H | H | H | H | Cl | $CO_2CH_2C\equiv CH$ | $CH_3$ | 1 | CHF | |
| H | H | H | H | F | Cl | $CO_2CH_2C\equiv CH$ | $CH_3$ | 1 | CHF | |
| H | H | H | H | F | Cl | $CO_2CH(CH_3)C\equiv CH$ | $CH_3$ | 1 | CHF | |
| H | H | H | H | F | Cl | $CO_2CH_2CH\equiv CH_2$ | $CH_3$ | 1 | CHF | |
| H | H | H | H | H | H | $CO_2CH_2C\equiv CH$ | $CH_3$ | 1 | CHCl | |
| H | H | H | H | H | Cl | $CO_2CH_2C\equiv CH$ | $CH_3$ | 1 | CHCl | |
| H | H | H | H | F | Cl | $CO_2CH_2C\equiv CH$ | $CH_3$ | 1 | CHCl | |
| H | H | H | H | F | Cl | $CO_2CH(CH_3)C\equiv CH$ | $CH_3$ | 1 | CHCl | |
| H | H | H | H | F | Cl | $CO_2CH_2C=CH_2$ | $CH_3$ | 1 | CHCl | |
| H | H | H | H | F | Cl | $CO_2(CH_2)_3CH_3$ | $CH_3$ | 2 | $CF_2$ | |
| H | H | H | H | F | Cl | $CO_2CH_2CH_2CH_3$ | $CH_3$ | 1 | $CF_2$ | |
| H | H | H | H | F | Cl | $CO_2CH_2CH_3$ | $CH_3$ | 1 | $CF_2$ | |
| H | H | H | H | F | Cl | $CO_2CH_3$ | $CH_3$ | 1 | $CF_2$ | |
| H | H | H | H | F | Cl | $CO_2(CH_2)_3CH_3$ | $CH_3$ | 1 | $CF_2$ | |
| H | H | H | H | Cl | Cl | $CO_2(CH_2)_3CH_3$ | $CH_3$ | 1 | $CF_2$ | |

Formulations

Appropriate formulations using compounds of the formula I can be prepared by conventional methods, in the form of powders, granules, pellets, solutions, suspensions, emulsions, wettable powders, emulsifiable concentrates, etc. Many of these forms may be applied directly. Sprayable preparations may be diluted with appropriate media and applied by spraying at a rate of between a few and a few hundred liters per hectare. Highly concentrated preparations are mainly used as intermediates for other formulations. The formulations contain, in very approximate terms, between 0.1 and 99 wt. % of active substance(s) and at least one member from the group a) 0.1 to 20% of surface-active substance and b) about 1 to 99.9% solid or liquid diluents. More accurately, these constituents are present in approximately the following amounts:

| | Active substance | wt. %*⁾ Diluent | Surface-active substance |
|---|---|---|---|
| Wetted powders | 20–90 | 0–74 | 1–10 |
| Suspensions in oil, emulsions, solutions, (inc. emulsifiable concentrates) | 3–50 | 40–95 | 0–15 |
| Aqueous suspensions | 10–50 | 40–84 | 1–20 |
| Dusts | 1–25 | 70–99 | 0–5 |
| Granules and pellets | 0.1–95 | 5–99.5 | 0–15 |
| Highly conc. preparations | 90–99 | 0–10 | 0–2 |

*⁾Active substance plus at least one surface active substance or one diluent = 100 wt. %

Smaller or larger amounts of active substance may naturally be present, depending on the intended application and the physical properties of the compound. Larger ratios by weight of surface-active component to active substance are sometimes desirable and are achieved by incorporation in the formulation or by mixing in a container.

Typical solid diluents are described in Watkins, et al., "Handbook of Insecticide Dust Diluents and Carriers" (Handbuch der Verdünnungsmittel und Träger staubförmiger Insektizide), 2nd ed., Dorland Books, Caldwell, N.J., but other solids, either mined or industrially produced, may also be used. In the case of wettable powders, the more absorbent diluents, and in the case of dusts, the more dense diluents, are preferred. Typical liquid diluents and solvents are described in Marsden, "Solvents Guide" (Lösemittelführer), 2nd ed., Interscience, New York, 1950. Less than 0.1% is preferred for concentrated suspensions. Concentrated solutions are preferably resistant to phase separation at 0° C. "McCutcheon's detergents and emulsifiers annual" (McCutcheon's Jahrbuch der Detergentien und Emulgatoren), MC Publishing Corp., Ridgewood, N.J., and Sisely and Wood, "Encyclopedia of Surface Active Agents" (Enzyclopädie der oberflächenaktiven Stoffe), Chemical Publishing Co. Inc., New York, 1964, contain lists of surface-active substances and the applications for which these are recommended. All formulations may contain relatively small amounts of additives to reduce the formation of foam, or to inhibit caking, corrosion or the growth of microorganisms, etc.

Methods for producing such preparations are well known. Solutions are prepared by simply mixing the constituents. Finely powdered solid preparations are obtained by mixing and, usually, milling, for example in a hammer mill or a jet mill. Suspensions are obtained by wet milling (see e.g. Littler, U.S. Pat. No. 3,060,084). Granules and pellets can be prepared by spraying the active substance onto pre-shaped, granular carriers or by agglomeration. For this, see J. E. Browning, "Agglomeration", Chemical Engineering, Dec. 4, 1967, p. 147 et seq. and "Perry's Chemical Engineer's Handbook" (Perry's Handbuch des chemischen Verfarhrenstechnikers), 5th ed., McGraw Hill, New York, 1973, p. 8-57 et seq.

For further information relating to formulation procedures, see e.g.:

H. M. Loux, U.S. Pat. No. 3,235,361, 15th Feb., 1966, column 6, line 16 to column 7, line 19 and examples 10 to 41;

R. W. Luckenbaugh, U.S. Pat. No. 3,309,192, 14th Mar. 1967, column 5, line 43 to column 7 line 62 and examples 8, 12, 15, 39, 41, 52, 53, 58, 132, 138-140, 162-164, 166, 167 and 169-182;

H. Gysin and E. Knusli, U.S. Pat. No. 2,891,855, 23rd Jun. 1959, column 3, line 66 to column 5, line 17 and examples 1-4;

G. C. Klingman, "Weed Control as a Science" (Unkrautbekämpfung als Wissenschaft), John Wiley and Sons, Inc., New York, 1961, p. 81-96 and J. D. Fryer and S. A Evans, "Weed Control Handbook" (Handbuch der Unkrautbekämpfung) 5th ed., Blackwell Scientific Publications, Oxford, 1968, p. 101-103.

In the following examples, the numbers refer to parts by weight, if no other data is given.

Example A

Wettable powder
5-(4-chlorophenyl)-4,6-dioxo-1,5-diazabicyclo-[4.4.0]-decane 80%
Sodium alkylnaphthlene sulphonate 2%
Sodium lignosulphonate 2%
Synthetic amorphous silica 3%
Kaolinite 13%

The constituents are mixed and then milled in a hammer mill until all the solid matter has a particle size essentially less than 50 μm, when it is re-mixed and packaged.

Example B

Wettable powder
5-(4-chlorophenyl)-4,6-dioxo-1,5-diazabicyclo-[4.4.0]-decane 50%
Sodium alkylnaphthalene sulphonate 2%
Low viscosity methyl cellulose 2%
Diatomaceous earth 46%

The constituents are mixed, coarsely crushed in a hammer mill and then milled in a jet mill so that virtually all the particles have a diameter of less than 10 μm. The product is then re-mixed before packaging.

Example C

Granules
Wettable powder from example B 5%
Attapulgite granules 95%
(USS 20-40 mesh; 0.84-0.42 mm)

A slurry of wettable powder with a 25% solids content is sprayed into a double cone blender. The granules are then dried and packaged.

Example D

Extruded pellets
5-(4-chlorophenyl)-4,5-dioxo-1,5-diazabicyclo-[4.4.0]-decane 25%
Anhydrous sodium sulphate 10%
Crude calcium lignosulphonate 5%
Sodium alkylnaphthalene sulphonate 1%
Calcium/magnesium bentonite 59%

The constituents are mixed, milled in a hammer mill and then moistened with approximately 12% water. The mixture is extruded to form cylinders with a diameter of approximately 3 mm, which are cut into pellets with a length of approximately 3 mm. These can be used directly after drying. The dried pellets, however, can be crushed so that they pass through a USS no. 20 sieve (mesh 0.84 mm diameter). The granules remaining behind on USS sieve no. 40 (0.42 mm mesh diameter) can be packaged for use, while the fine fractions are returned.

Example E

Low strength granules
5-(4-chlorophenyl)-4,6-dioxo-1,5-diazabicyclo-[4.4.0]-decane 1%
N,N-dimethylformamide 9%
Attapugite granules 90%
(USS sieves 20 to 40)

The active substance is dissolved in the solvent and the solution is sprayed onto de-dusted granules in a double cone blender. After spraying the solution in, the mixer is run for only a short time, after which the granules are packaged.

Example F

Granules
5-(4-chlorophenyl)-4,6-dioxo-1,5-diazabicyclo-[4.4.0]-
   decane 80%
Wetting agent 1%
Crude lignosulphonate (with 5 to 20% of 10% natural sugar)
Attapulgite clay 9%

The components are mixed and milled until they pass through a 100 mesh sieve. This material is then introduced to a fluidised bed granulator, where the air current is adjusted so that the material is readily whirled up and wherein a fine jet of water is sprayed onto the swirling material. Fluidisation and spraying are continued until granules of the desired size are obtained. Spraying is then discontinued, while fluidisation on the other hand, optionally with the introduction of heat, is continued until the water content has fallen to the desired value, generally less than 1%. The material is then withdrawn and screened to the desired size range, usually 14 to 100 mesh (1410 to 149 μm), when it is packaged for use.

Example G

Aqueous suspension
5-(4-chlorophenyl)-4,6-dioxo-1,5-diazabicyclo-[4.4.0]-
   decane 40%
Thickening agent based on polyacrylic acid 0.3%
Dodecylphenol-polyethyleneglycol-ether 0.5%
Disodium phosphate 1%
Monosodium phosphate 0.5%
polyvinylalcohol 1.0%
water 56.7%

The constituents are mixed and milled together in a sand mill in order to obtain particles with a size of essentially less than 5 μm.

Example H

Strong concentrate
5-(4-chlorophenyl)-4,6-dioxo-1,5-diazabicyclo-[4.4.0]-
   decane 99%
Silica aerogel 0.5%
Synthetic amorphous silica 0.5%

The constituents are mixed and milled in a hammer mill in order to obtain a material which passes through a USS sieve no. 50 (0.3 mm mesh). The concentrate can, if required, contain other constituents.

Example I

Wettable powder
5-(4-chlorophenyl)-4,6-dioxo-1,5-diazabicyclo-[4.4.0]-
   decane 90.0%
Dioctyl sodium sulphocuccinate 0.1%
Synthetic fine silica 9.9%

The constituents are mixed and milled in a hammer mill in order to obtain particles with a size of essentially less than 100 μm. The material is screened on a USS no. 50 sieve and then packaged.

Example J

Wettable powder
5-(4-chlorophenyl)-4,6-dioxo-1,5-diazabicyclo-[4.4.0]-
   decane 40%
Sodium lignosulphonate 20%
Montmorillonite clay 40%

The constituents are thoroughly mixed, milled in a hammer mill and then milled in an air-jet mill in order to obtain particles with a size of essentially less than 10 μm. The material is then re-mixed and packaged.

Example K

Suspension in oil
5-(4-chlorophenyl )-4,6-dioxo-1,5-diazabicyclo- [4.4.0]-
   decane 35%
Mixture of polyalcohol/carboxylates and oil-soluble petroleum sulphonates 6%
Xylene 59%

The constituents are mixed and milled in a sand mill in order to obtain particles with a size of essentially less than 5 μm. The product can be used directly, diluted with oil or emulsified in water.

Example L

Dust
5-(4-chlorophenyl)-4,6-dioxo-1,5-diazabicyclo-[4.4.0]-
   decane 10%
Attapulgite 10%
Pyrophillite 80%

The active substance is mixed with attapulgite and then placed in a hammer mill in order to obtain particles with a size of essentially less than 200 μm. The milled concentrate is then mixed with powdered pyrophillite until the mixture is homogenous.

Example M

Suspension in oil
5-(4-chlorophenyl)-4,6-dioxo-1,5-diazabicyclo-[4.4.0]-
   decane 25%
Polyoxyethylenesorbitol hexaoleate 5%
Highly aliphatic hydrocarbon oil 70%

The constituents are mixed together in a sand mill until the size of the solid particles is less than about 5 μm. The resulting thick suspension can be used directly. Preferably, however, it is used after diluting with oils or after emulsifying in water.

Biological examples

Trial results show that the compounds according to the present invention are effective herbicides. They are suitable for broad-band control of weeds before and after germination in areas where the whole vegetation is intended to be kept under control, for example in the vicinity of industrial storage areas, car parks, drive-in cinemas hoardings, roads and railway structures. Many of the compounds are also suitable for selective weed control when cultivating, for instance, rice, wheat, barley, maize, soy beans, sugar beet and cotton.

The amount of compounds according to the present invention to be applied depends on numerous factors including its use as a selective or universal herbicide, the particular agricultural crop, the type of weed to be controlled, the weather and climate, the formulation selected, the method of application, the amount of foliate vegetation etc. In general, the compounds should be applied in amounts between 0.001 and 20 kg/ha, wherein the smaller amounts are suitable for lighter soils and/or soils with low concentrations of organic substances or in the event that only short residence times are required such as in the case of herbicides for fallow land.

The compounds according to the invention may be used in combination with any other commercially available herbicide.

The herbicidal properties of the compounds according to the present invention were discovered in a series of hothouse trials. The test method and results are given in the following.

Biological Tables

Compound 1
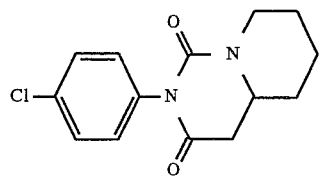

Compound 2
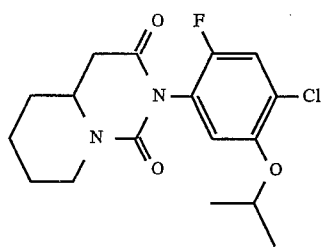

Compound 3
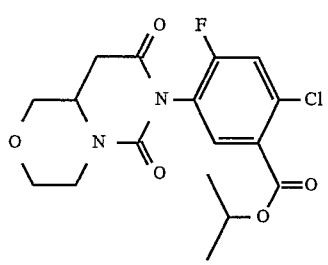

Compound 4
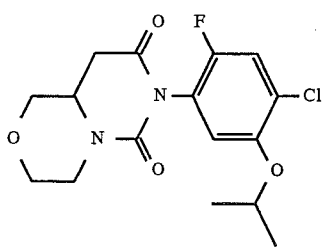

Compound 5
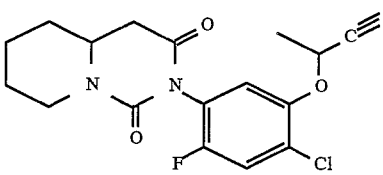

Compound 6
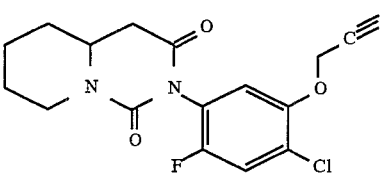

Compound 7
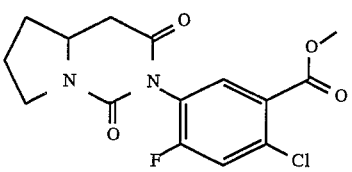

-continued
Biological Tables

Compound 8
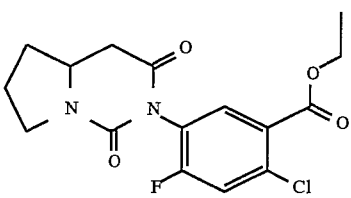

Compound 9
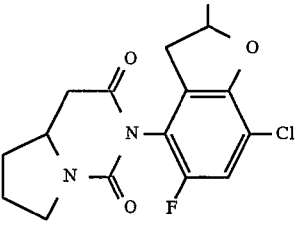

Compound 10
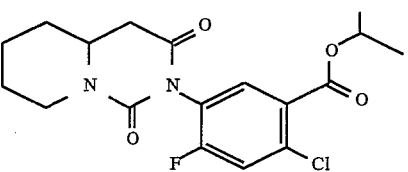

Compound 11
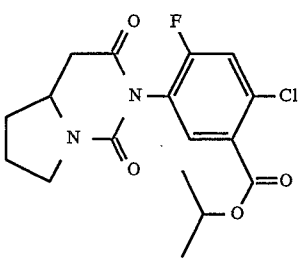

Compound 12
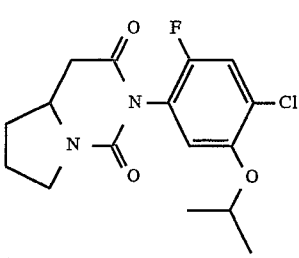

Test Method

Seeds of digitaria spp, echinochloa crus-galli, setaria feberii, avena fatua, bromus secalinus, abutilon theophrasti, ipomoea spp., xanthium pensylvanicum and Sorghum-Knollen were used and treated, before germination, with the trial chemical dissolved in a non-phytotoxic solvent.

In addition, these weeds were treated with a preparation specified for soil and for foliage. The plants were 2 to 18 cm tall at the time they were treated. The treated plants and the control plants were kept for 16 days in a hothouse, then all specimens were kept with the control plants for 16 days in the hothouse, after which all specimens were compared with the control plants and the effect of the treatment was assessed visually. The evaluations summarised in Table A are based on a numerical scale from 0=no damage to 10=complete destruction.

The symbols alongside the numbers indicate the following:

C=chlorosis/necrosis
B=burning effect
H=deforming effect

E=germination inhibited

G=growth stimulated

TABLE A

Application after germination
(Dose of 2 kg of active substance per ha)

| Object | Comp. 1 | Comp. 2 | Comp. 3 | Comp. 4 | Comp. 5 |
|---|---|---|---|---|---|
| Echinochloa c–g | 3B | 10B | 10C | 10C | 10 |
| Bromus secalinus | 2B | 8B | 10C | 10C | 10 |
| Xanthium pens. | 2B | 8B | 10C | 9C | 10 |
| Ipomoea spp. | 9B | 10B | 10C | 10C | 10 |
| Sorghum | 4B | 10B | 10C | 9C | 10 |
| Setaria feberii | 4B | 10B | 10C | 10C | 10 |
| Digitaria spp. | 3B | 9B | 10C | 10C | 10 |
| Abutilon th. | 10B | 10B | 10C | 10C | 10 |
| Avena fatua | 2B | 2B | 10C | 9C | 10 |

| Object | Comp. 6 | Comp. 7 | Comp. 8 | Comp. 9 |
|---|---|---|---|---|
| Echinochloa c–g | 10 | 10 | 10 | 10 |
| Bromus secalinus | 10 | 10 | 10 | 10 |
| Xanthium pens. | 10 | 10 | 10 | 10 |
| Ipomoea spp. | 10 | 10 | 10 | 10 |
| Sorghum | 10 | 10 | 10 | 10 |
| Setaria feberii | 10 | 10 | 10 | 10 |
| Digitaria spp. | 10 | 10 | 10 | 10 |
| Abutilon th. | 10 | 10 | 10 | 10 |
| Avena fatua | 10 | 10 | 10 | 10 |

TABLE B

Application before germination
(Dose 2 kg active substance/ha)

| Object | Comp. 1 | Comp. 2 | Comp. 3 | Comp. 4 | Comp. 5 |
|---|---|---|---|---|---|
| Echinochloa c–g | 7H, 3C | 10C | 10C | 10C | 10 |
| Bromus secalinus | 3C | 9C | 10C | 10C | 10 |
| Xanthium pens. | — | — | 10C | 10C | 10 |
| Ipomoea spp. | 8C | 10C | 10C | 10C | 10 |
| Sorghum | 10C | 10C | 10C | 10C | 10 |
| Setaria feberii | 9C | 10C | 10E | 10E | 10 |
| Digitaria spp. | 10C | 10C | 10E | 10C | 10 |
| Abutilon th. | 10C | 10C | 10E | 10E | 10 |
| Avena fatua | 2C | 9H, 4C | 10C | 10C | 10 |

| Object | Comp. 6 | Comp. 7 | Comp. 8 | Comp. 9 |
|---|---|---|---|---|
| Echinochloa c–g | 10 | 10 | 10 | 10 |
| Bromus secalinus | 10 | 10 | 10 | 10 |
| Xanthium pens. | 10 | 10 | 10 | 10 |
| Ipomoea spp. | 10 | 10 | 10 | 10 |
| Sorghum | 10 | 10 | 10 | 10 |
| Setaria feberii | 10 | 10 | 10 | 10 |
| Digitaria spp. | 10 | 10 | 10 | 10 |
| Abutilon th. | 10 | 10 | 10 | 10 |
| Avena fatua | 10 | 10 | 10 | 10 |

TABLE C

Application after germination
(Dose 0.2 kg active substance per ha)

| Object | Comp. 10 | Comp. 11 | Comp. 12 |
|---|---|---|---|
| Wheat | 3B | 9B | 4B |
| Soy beans | 2B | 10B | 8B |
| Echinochloa c–g | 8B | 10B | 7B |

TABLE C-continued

Application after germination
(Dose 0.2 kg active substance per ha)

| Object | Comp. 10 | Comp. 11 | Comp. 12 |
|---|---|---|---|
| Bromus secalinus | 3B, 3G | 9B | 4B |
| Xanthium pens. | 9B | 10B | 7B |
| Ipomoea spp. | 10B | 10B | 8B |
| Sorghum | 3B | 10B | 7B |
| Setaria feberii | 8B | 10B | 9B |
| Digitaria spp. | 4G, 2B | 10B | 9H, 6B |
| Abutilon th. | 10B | 10B | 10B |
| Avena fatua | 3B, 3G | 9B | 5B |

TABLE D

Application before germination
(Dose 0.2 kg of active substance per ha)

| Object | Comp. 10 | Comp. 11 | Comp. 12 |
|---|---|---|---|
| Wheat | 0 | 2C | 2C |
| Soy beans | 2C | 2C | 2C |
| Echinochloa c–g | 9G, 5C | 10C | 9C |
| Bromus secalinus | 7G, 4C | 10C | 4G, 2C |
| Xanthium pens. | 10C | 5C | 3H, 2C |
| Ipomoea spp. | 10C | 4C | 8G, 2C |
| Sorghum | 7H, 4C | 10C | 6H, 3C |
| Setaria feberii | 10E | 10C | 10C |
| Digitaria spp. | 10E | 10C | 10C |
| Abutilon th. | 10E | 10C | 10C |
| Avena fatua | 6H, 3C | 9C | 4C |

What is claimed is:

1. Heterocyclic compounds of the formula I, in which

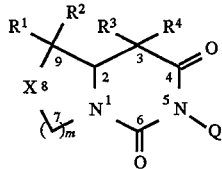

I

X represents $CH_2$, CHF, $CF_2$, CHCl, CHBr, $CHOCHF_2$, $CHOCF_3$ or $CHOCH_2CF_3$, m represents 1

$R^1$ and $R^2$, independently of each other, represent hydrogen, hydroxy, a halogen, or a $(C_1-C_4)$-alkyl, $(C_1-C_4)$-alkoxy, $(C_1-C_4)$-haloalkyl or $(C_1-C_4)$-haloalkoxy group, $R^3$ and $R^4$, independently of each other, represent hydrogen, hydroxy, a halogen, cyanogen, a $(C_1-C_4)$-alkyl, $(C_1-C_4)$-haloalkyl, $(C_3-C_4)$-alkenyl, $(C_3-C_4)$-haloalkenyl, $(C_1-C_4)$-alkoxy, $(C_2-C_6)$-alkoxycarbonyl, or $(C_3-C_8)$-alkoxycarbonylalkyl group or phenyl or benzyl, both optionally substituted by halogen or a $(C_1-C_4)$-alkyl or $(C_1-C_4)$-alkoxy group, Q represents one of the groups Q-1–Q-7,

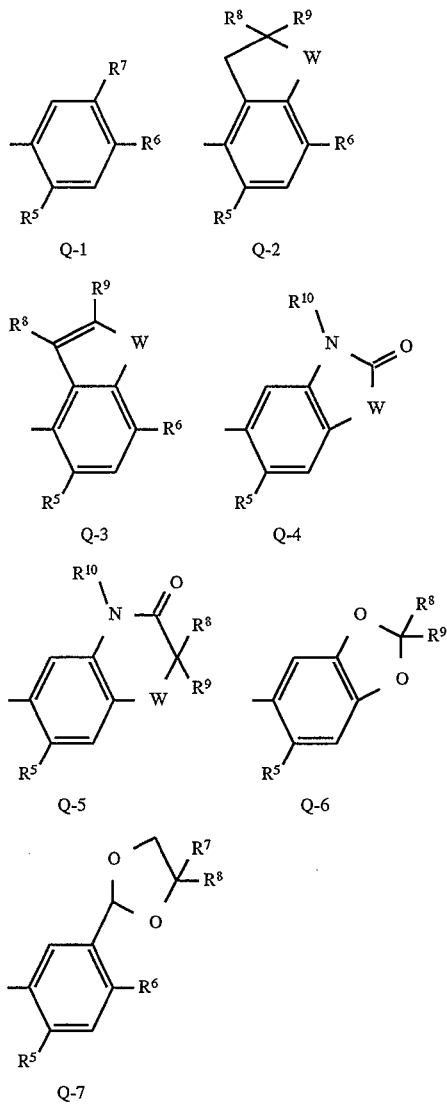

in which

W represents O or S, $R^5$ represents hydrogen or a halogen, $R^6$ represents a $(C_1-C_2)$-alkyl or $(C_1-C_2)$-haloalkyl group, $OCH_3$, $SCH_3$, $OCHF_2$, a halogen, CN or $NO_2$, $R^7$ represents hydrogen or a $(C_1-C_8)$-alkyl or $(C_1-C_8)$-haloalkyl group, a halogen, $OR^{11}$, $S(O)_nR^{11}$, $COR^{11}$, $CO_2R^{11}$, $C(O)SR^{11}$, $C(O)NR^{12}R^{13}$, CHO, $CH=CHCO_2R^{11}$, $CO_2N=CR^{14}R^{15}$, $NO_2$, CN, $NHSO_2R^{16}$ or $NHSO_2NHR^{16}$, $R^8$ represents hydrogen, a $(C_1-C_3)$-alkyl or $(C_1-C_3)$-haloalkyl group or a halogen, $R^9$ represents hydrogen, a $(C_1-C_3)$-alkyl or $(C_1-C_3)$-haloalkyl group or a halogen; or, when Q is Q-2 or Q-6, $R^8$ and $R^9$, together with the carbon atom to which they are bonded, may be C=O, $R^{10}$ represents a $(C_1-C_6)$-alkyl, $(C_1-C_6)$-haloalkyl, $(C_2-C_6)$-alkoxyalkyl, $(C_3-C_6)$-alkenyl or $(C_3-C_6)$-alkynyl group, $R^{11}$ represents a $(C_1-C_8)$-alkyl, $(C_3-C_8)$-cycloalkyl, $(C_3-C_8)$-alkenyl, $(C_3-C_8)$-alkynyl, $(C_1-C_8)$-haloalkyl, $(C_2-C_8)$-alkoxyalkyl, $(C_2-C_8)$-alkylthioalkyl, $(C_2-C_8)$-alkylsulphinylalkyl, $(C_2-C_8)$-alkylsulphonylalkyl, $(C_4-C_8)$-alkoxyalkoxyalkyl, $(C_4-C_8)$-cycloalkylalkyl, $(C_2-C_4)$-carboxyalkyl, $(C_3-C_8)$-alkoxycarbonylalkyl, $(C_6-C_8)$-alkenyloxycarbonylalkyl $(C_6-C_8)$-alkynyloxycarbonylalkyl, $(C_4-C_8)$-alkenoxyalkyl, $(C_6-C_8)$-cycloalkoxyalkyl, $(C_4-C_8)$-alkynyloxyalkyl, $(C_3-C_8)$-haloalkoxyalkyl, $(C_4-C_8)$-haloalkenyloxyalkyl, $(C_4-C_8)$-haloalkynyloxyalkyl, $(C_6-C_8)$-cycloalkylthioalkyl, $(C_4-C_8)$-alkenylthioalkyl, $(C_4-C_8)$-alkynylthioalkyl, $(C_1-C_4)$-alkyl substituted with phenoxy or benzyloxy, both optionally substituted with halogen or a $(C_1-C_3)$-alkyl or $(C_1-C_3)$-haloalkyl group, $(C_4-C_8)$-trialkylsilylalkyl, $(C_3-C_8)$-cyanoalkyl, $(C_3-C_8)$-halocycloalkyl, $(C_3-C_8)$-haloalkenyl, $(C_5-C_8)$-alkoxyalkenyl, $(C_5-C_8)$-haloalkoxyalkenyl, $(C_5-C_8)$-alkylthioalkenyl, $(C_3-C_8)$-haloalkynyl, $(C_5-C_8)$-alkoxyalkynyl, $(C_5-C_8)$-haloalkoxyalkynyl, $(C_5-C_8)$-alkylthioalkynyl or $(C_2-C_8)$-alkylcarbonyl group, benzyl, optionally substituted with halogen or a $(C_1-C_3)$-alkyl or $(C_1-C_3)$-haloalkyl group, $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CR^{17}C(O)NH_2$, phenyl or pyridyl, both optionally substituted with halogen or a $(C_1-C_3)$-alkyl, $(C_1-C_3)$-haloalkyl or $(C_1-C_4)$-alkoxy group, $R^{12}$ and $R^{14}$, independently of each other, represent hydrogen or a $(C_1-C_4)$-alkyl group, $R^{13}$ and $R^{15}$, independently of each other, represent a $(C_1-C_4)$-alkyl group or phenyl, optionally substituted with halogen or a $(C_1-C_3)$-alkyl, $(C_1-C_3)$-haloalkyl or $(C_1-C_4)$-alkoxy group, $R^{12}$ and $R^{13}$, when they are —$(CH_2)_5$—, —$(CH_2)_4$— or —$CH_2CH_2OCH_2CH_2$—, may be combined to give rings, wherein one or more H atoms in each ring may optionally be substituted by a $(C_1-C_3)$-alkyl group, phenyl or benzyl, $R^{14}$ and $R^{15}$, together with the carbon atom to which they are bonded, may form a $(C_3-C_8)$-cycloalkyl group, $R^{16}$ represents a $(C_1-C_4)$-alkyl or $(C_1-C_4)$-haloalkyl group, $R^{17}$ represents hydrogen or a $(C_1-C_3)$-alkyl group, $R^{18}$ represents a $(C_1-C_6)$-alkyl, $(C_3-C_6)$-alkenyl or $(C_3-C_6)$-alkynyl group and n represents 0, 1 or 2.

2. Heterocyclic compounds of the formula I, in accordance with claim 1, characterised in that in at least one of the groups X represents $CH_2$, CHF, $CF_2$, CHCl, CHBr, $CHOCHF_2$, $CHOCF_3$ or $CHOCH_2CF_3$, m represents 1

$R^1$ and $R^2$, independently of each other, represent hydrogen, hydroxy, fluorine, chlorine, bromine, methyl or methoxy, $R^3$ and $R^4$, independently of each other, represent hydrogen, hydroxy, fluorine, chlorine, bromine, cyanogen, a $(C_1-C_2)$-alkyl, $(C_1-C_2)$-haloalkyl, $(C_3-C_4)$-alkenyl, $(C_3-C_4)$-haloalkenyl or $(C_1-C_2)$-alkoxy group or phenyl or benzyl, both optionally substituted with fluorine, chlorine, bromine, methyl or methoxy, w represents O or S, n represents 0, 1 or 2, $R^5$ represents hydrogen or a halogen, $R^6$ represents a halogen or CN, $R^7$ represents hydrogen, a $(C_1-C_4)$-alkyl or $(C_1-C_4)$-haloalkyl group, a halogen, $OR^{11}$, $S(O)_nR^{11}$, $COR^{11}$, $CO_2R^{11}$, $C(O)SR^{11}$, $C(O)NR^{12}R^{13}$, $CH=CHCO_2R^{11}$, $CO_2N=CR^{14}R^{15}$, $NHSO_2R^{16}$ or $NHSO_2NHR^{16}$, $R^8$ represents hydrogen or a $(C_1-C_3)$-alkyl or $(C_1-C_3)$-haloalkyl group, $R^9$ represents hydrogen or a $(C_1-C_3)$-alkyl or $(C_1-C_3)$-haloalkyl group, or, when Q=Q-2 or Q-6, $R^8$ and $R^9$, together with the carbon to which they are bonded, may be C=O, $R^{10}$ represents a $(C_1-C_4)$-alkyl, $(C_1-C_4)$-haloalkyl, $(C_2-C_4)$-alkoxyalkyl, $(C_3-C_6)$-alkenyl or $(C_3-C_6)$-alkynyl group, $R^{11}$ represents a $(C_1-C_4)$-alkyl, $(C_3-C_6)$-cycloalkyl, $(C_3-C_6)$-alkenyl, $(C_3-C_6)$-alkynyl, $(C_1-C_4)$-haloalkyl, $(C_2-C_4)$-alkoxyalkyl, $(C_2-C_4)$-alkylthioalkyl, $(C_2-C_4)$-alkylsulphinylalkyl, $(C_2-C_4)$-alkylsulphonylalkyl, $(C_3-C_6)$-alkoxyalkoxyalkyl, $(C_4-C_8)$-cycloalkylalkyl, $(C_2-C_4)$-carboxyalkyl, $(C_3-C_6)$-alkoxycarbonylalkyl, $(C_6-C_8)$-alkenyloxycarbonylalkyl $(C_6-C_8)$-alkynyloxycarbonylalkyl, $(C_4-C_6)$-alkenoxyalkyl, $(C_6-C_8)$-cycloalkoxyalkyl, $(C_4-C_6)$-alkynyloxyalkyl, $(C_3-C_6)$-haloalkoxyalkyl, $(C_4-C_8)$-haloalkenyloxyalkyl, $(C_4-C_6)$-haloalkynyloxyalkyl, $(C_6-C_8)$-cycloalkylthioalkyl, $(C_4-C_6)$-alkenylthioalkyl, $(C_4-C_6)$-alkynylthioalkyl, $(C_1-C_2)$-alkyl substituted with phenoxy or benzyloxy, both optionally substituted with halogen or a $(C_1-C_3)$-alkyl or $(C_1-C_3)$-haloalkyl group, $(C_4-C_8)$-trialkylsilylalkyl, $(C_3-C_4)$-cyanoalkyl, $(C_3-C_6)$-halocycloalkyl, $(C_3-C_6)$-haloalkenyl, $(C_5-C_6)$-haloalkoxyalkenyl, $(C_5-C_6)$-alkylthioalkenyl, $(C_3-C_6)$-haloalkynyl, $(C_5-C_6)$-alkoxyalkynyl, $(C_5-C_6)$-haloalkoxyalkynyl, $(C_5-C_6)$-alkylthioalkynyl or $(C_2-C_4)$-alkylcarbonyl group, benzyl, optionally substituted with halogen or a $(C_1-C_2)$-alkyl or $(C_1-C_2)$-haloalkyl group, $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CR^{17}C(O)NH_2$, phenyl or pyridyl, both optionally substituted with halogen or a $(C_1-C_3)$-alkyl, $(C_1-C_3)$-haloalkyl or $(C_1-C_4)$-alkoxy group, $R^{12}$ and $R^{14}$, independently of each other, represent hydrogen or a $(C_1-C_2)$-alkyl group, $R^{13}$ and $R^{15}$, independently of each other, represent a $(C_1-C_2)$-alkyl group or phenyl, optionally substituted with halogen or a $(C_1-C_2)$-alkyl, $(C_1-C_2)$-haloalkyl or $(C_1-C_2)$-alkoxy group, $R^{12}$ and $R^{13}$, when they are $—(CH_2)_5—$, $—(CH_2)_4—$ or $—CH_2CH_2OCH_2CH_2—$, may be combined to give rings, wherein one or more H atoms in each ring may optionally be substituted by a $(C_1-C_2)$-alkyl group, phenyl or benzyl, $R^{14}$ and $R^{15}$, together with the carbon atom to which they are bonded, may form a $(C_3-C_6)$-cycloalkyl group, $R^{16}$ represents a $(C_1-C_4)$-alkyl or $(C_1-C_4)$-haloalkyl group, $R^{17}$ represents hydrogen or a $(C_1-C_3)$-alkyl group and $R^{18}$ represents a $(C_1-C_4)$-alkyl, $(C_3-C_4)$-alkenyl or $(C_3-C_4)$-alkynyl group.

3. Heterocyclic compounds of the formula I, in accordance with claim 1, characterised in that in at least one of the groups X represents $CH_2$, m represents 1, $R^1$ and $R^2$ represent hydrogen, $R^3$ and $R^4$ represent hydrogen, w represents O or S, $R^5$ represents hydrogen, fluorine or chlorine, $R^6$ represents chlorine, bromine or cyanogen, $R^7$ represents hydrogen, $OR^{11}$ or $CO_2R^{11}$, $R^8$ and $R^9$, independently of each other, represent hydrogen or a $(C_1-C_2)$-alkyl or $(C_1-C_2)$-haloalkyl group, $R^{10}$ represents a $(C_1-C_2)$-alkyl, $(C_1-C_2)$-haloalkyl, $(C_3-C_4)$-alkenyl or $(C_3-C_4)$-alkynyl group, $R^{11}$ represents a $(C_1-C_4)$-alkyl, $(C_3-C_6)$-cycloalkyl, $(C_3-C_6)$-alkenyl, $(C_3-C_6)$-alkynyl, $(C_1-C_4)$-haloalkyl, $(C_2-C_4)$-alkoxyalkyl, $(C_2-C_4)$-alkylthioalkyl, $(C_2-C_4)$-alkylsulphinylalkyl, $(C_2-C_4)$-alkylsulphonylalkyl, $(C_3-C_6)$-alkoxyalkoxyalkyl, $(C_4-C_8)$-cycloalkylalkyl, $(C_2-C_4)$-carboxyalkyl, $(C_3-C_6)$-alkoxycarbonylalkyl, $(C_6-C_8)$-alkenyloxycarbonylalkyl $(C_6-C_8)$-alkynyloxycarbonylalkyl, $(C_6-C_8)$-cycloalkoxyalkyl, $(C_4-C_6)$-alkenyloxyalkyl, $(C_4-C_6)$-alkynyloxyalkyl, $(C_3-C_6)$-haloalkoxyalkyl, $(C_4-C_8)$-haloalkenoxyalkyl, $(C_4-C_6)$-haloalkynyloxyalkyl, $(C_6-C_8)$-cycloalkylthioalkyl, $(C_4-C_6)$-alkenylthioalkyl, $(C_4-C_6)$-alkynylthioalkyl, $(C_1-C_2)$-alkyl substituted with phenoxy or benzyloxy, both optionally substituted with halogen or a $(C_1-C_3)$-alkyl or $(C_1-C_3)$-haloalkyl group, $(C_4-C_8)$-trialkylsilylalkyl, $(C_3-C_4)$-cyanoalkyl, $(C_3-C_6)$-halocycloalkyl, $(C_3-C_6)$-haloalkenyl, $(C_5-C_6)$-alkoxyalkenyl, $(C_5-C_6)$-haloalkoxyalkenyl, $(C_5-C_6)$-alkylthioalkenyl, $(C_3-C_6)$-haloalkynyl, $(C_5-C_6)$-alkoxyalkynyl, $(C_5-C_6)$-haloalkoxyalkynyl, $(C_5-C_6)$-alkylthioalkynyl or $(C_2-C_4)$-alkylcarbonyl group, benzyl, optionally substituted with halogen or a $(C_1-C_2)$-alkyl or $(C_1-C_2)$-haloalkyl group, $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CR^{17}C(O)NH_2$, phenyl or pyridyl, both optionally substituted with fluorine, chlorine or bromine or a $(C_1-C_2)$-haloalkyl or $(C_1-C_2)$-alkoxy group, $R^{12}$ represents hydrogen or a $(C_1-C_2)$-alkyl group, $R^{13}$ represents a $(C_1-C_2)$-alkyl group, phenyl, optionally substituted with fluorine, chlorine, bromine or a $(C_1-C_2)$-alkyl, $(C_1-C_2)$-haloalkyl or $(C_1-C_2)$-alkoxy group, $R^{12}$ and $R^{13}$, when they are $—(CH_2)_5—$, $—(CH_2)_4—$ or $—CH_2CH_2OCH_2CH_2—$, may be combined to give rings, wherein one or more H atoms in each ring may optionally be substituted by a $(C_1-C_2)$-alkyl group, $R^{17}$ represents hydrogen or a $(C_1-C_2)$-alkyl group and $R^{18}$ represents a $(C_1-C_2)$-alkyl, $(C_3-C_4)$-alkenyl or $(C_3-C_4)$ alkynyl group.

4. Heterocyclic compounds of the formula I, in accordance with claim 1, characterised in that in at least one of the groups X represents $CH_2$, m represents 1 or 2, $R^1$ and $R^2$ represent hydrogen, $R^3$ and $R^4$ represent hydrogen, $R^5$ represents fluorine or chlorine, $R^6$ represents chlorine, $R^7$ represents $OR^{11}$ or $CO_2R^{11}$ and $R^{11}$ represents a $(C_1-C_4)$-alkyl, $(C_3-C_6)$-cycloalkyl, $(C_3-C_6)$-alkenyl, $(C_3-C_4)$-alkynyl, $(C_1-C_3)$-haloalkyl, $(C_2-C_4)$-alkoxyalkyl, $(C_3-C_6)$-alkoxycarbonylalkyl, $(C_6-C_8)$-alkenyloxycarbonylalkyl or $(C_6-C_8)$-alkynyloxycarbonyl group.

5. A herbicidal composition comprising a compound in accordance with claim 1 and a carrier.

6. A process for weed control, said process comprising applying a herbicidally effective amount of a compound in accordance with claim 1 to weeds or to their surroundings.

* * * * *